United States Patent
Knox et al.

(10) Patent No.: US 9,545,340 B1
(45) Date of Patent: Jan. 17, 2017

(54) MULTI-PHOTON ABSORPTION FOR FEMTOSECOND MICROMACHINING AND REFRACTIVE INDEX MODIFICATION OF TISSUES

(75) Inventors: Wayne H. Knox, Pittsford, NY (US); Krystel R. Huxlin, Rush, NY (US); Li Ding, Rochester, NY (US)

(73) Assignee: University of Rochester, Rochester, NY (US)

( * ) Notice: Subject to any disclaimer, the term of this patent is extended or adjusted under 35 U.S.C. 154(b) by 1906 days.

(21) Appl. No.: 12/207,137

(22) Filed: Sep. 9, 2008

Related U.S. Application Data (63) Continuation-in-part of application No. 12/146,976, filed on Jun. 26, 2008, now Pat. No. 8,486,055.

(60) Provisional application No. 60/929,397, filed on Jun. 26, 2007, provisional application No. 61/026,890, filed on Feb. 7, 2008.

(51) Int. Cl.
*A61F 9/008* (2006.01)

(52) U.S. Cl.
CPC ....... *A61F 9/00804* (2013.01); *A61F 9/00827* (2013.01); *A61F 2009/0087* (2013.01); *A61F 2009/00872* (2013.01)

(58) Field of Classification Search
CPC ...................................................... A61F 9/008
See application file for complete search history.

(56) References Cited

U.S. PATENT DOCUMENTS

| | | | |
|---|---|---|---|
| 5,461,212 A | 10/1995 | Seiler et al. | |
| 5,779,696 A | 7/1998 | Berry et al. | |
| 5,849,006 A | 12/1998 | Frey et al. | |
| 6,261,220 B1 | 7/2001 | Frey et al. | |
| 6,270,221 B1 | 8/2001 | Liang et al. | |
| 6,271,914 B1 | 8/2001 | Frey et al. | |
| 6,478,792 B1 * | 11/2002 | Hansel | 606/5 |
| 8,486,055 B2 | 7/2013 | Knox et al. | |
| 8,617,147 B2 | 12/2013 | Knox et al. | |
| 8,901,190 B2 | 12/2014 | Smith et al. | |
| 9,060,847 B2 | 6/2015 | Smith et al. | |
| 2004/0102765 A1 | 5/2004 | Koenig | |
| 2004/0243111 A1 * | 12/2004 | Bendett | A61F 9/00827 606/5 |
| 2004/0243112 A1 | 12/2004 | Bendett et al. | |
| 2005/0185138 A1 | 8/2005 | Wong et al. | |

(Continued)

FOREIGN PATENT DOCUMENTS

| | | |
|---|---|---|
| WO | 2008002796 A2 | 1/2008 |
| WO | 2009003107 A1 | 12/2008 |

OTHER PUBLICATIONS

Born, M., & Wolf, E. (1970). Principle of Optics. Pergamon Press, Oxford.

(Continued)

*Primary Examiner* — Lynsey Crandall
(74) *Attorney, Agent, or Firm* — Andrew J. Anderson, Esq.; Harter Secrest & Emery LLP (57) ABSTRACT

By adapting femtosecond micromachining approaches developed in hydrogels, we can perform Intra-tissue Refractive Index Shaping (IRIS) in biological tissues. We reduced femtosecond laser pulse energies below the optical breakdown thresholds to create grating patterns that are associated with a change in the refractive index of the tissue. To increase two-photon absorption, we used a two (or more)-photon-absorbing chromophore.

27 Claims, 7 Drawing Sheets

(56) References Cited

U.S. PATENT DOCUMENTS

| | | |
|---|---|---|
| 2007/0055221 A1 | 3/2007 | Lubatschowski |
| 2008/0001320 A1* | 1/2008 | Knox ............... A61F 9/008 264/1.37 |
| 2008/0021443 A1 | 1/2008 | Bischoff et al. |
| 2009/0005764 A1 | 1/2009 | Knox et al. |
| 2009/0287306 A1 | 11/2009 | Smith et al. |
| 2010/0292676 A1* | 11/2010 | Larsen ............... A61F 9/008 606/4 |
| 2011/0071509 A1 | 3/2011 | Knox et al. |

OTHER PUBLICATIONS

Brazitikos, P.D., D'Amico, D.J., Bochow, T.W., Hmelar, M., Marcellino, G.R., & Stangos, N.T. (1998). Experimental Ocular Surgery with a High-Repetition-Rate Erbium: YAG Laser. *Investigative Ophthalmology and Visual Science*, 39(9), 1667-1675.

Davis, K.M., Miura, K., Sugimoto, N., & Hirao, K. (1996). Writing waveguides in glass with a femtosecond laser. Opt. Lett., 21, 1729-1731.

Day, D., & Gu, M. (2005). Microchannel fabrication in PMMA based on localized heating by nonojoule high repetition rate femtosecond pulses. *Opt. Express*, 13, 5939-5946.

Ding, L., Blackwell, R., Kunzler, J.F., & Knox, W.H. (2006). Large refractive index change in silicone-based and non-siliconed-based hydrogel polymers induced by femtosecond laser micro-machinig. *Optics Express*, 14 (24), 11901-11909.

Ding, L., Knox, W.H., Bühren, J., Nagy, L.J., & Huxlin, K.R. (2008). Intra-tissue Refractive Index Shaping (IRIS) of the cornea and lens using a low-pulse-energy femtosecond laser oscillator. *Investigative Ophthalmolgy and Visual Science, in press.*

Docchio, F., Sacchi, C.A., & Marshall, J. (1986). Experimental investigation of optical breakdown thresholds in ocular media under single pulse irradiation with different pulse durations. *Lasers Ophthalmol*, 1, 83-93.

Du, D., Liu, X., Korn, G., Squier, J.A., & Mourou, G. (1994). Laser induced breakdown by impact ionization in SiO2 with pulse widths from 7 ns to 150 fs. *Applied Physics Letters*, 64, 3071-3073.

Eaton, S.M., Zhang, H., Herman, P.R., Yoshino, F., Shah, L., Bovatsek, J., & Arai, A.Y. (2005a). Heat accumulation effects in femtosecond laser-written waveguides with variable repetition rate. *Optics Express*, 13, 4708-4716.

Eaton, S.M., Zhang, H., Herman, P.R., Yoshino, F., Shah, L., Bovatsek, J., & Arai, A.Y. (2005b). Heat accumulation effects in femtosecond laser-written waveguides with variable repetition rate. *Opt. Express*, 13, 4708-4716.

Fisher, B.T., Masiello, K.A., Goldstein, M.H., & Hahn, D.W. (2003). Assessment of transient changes in corneal hydration using confocal Raman spectroscopy. *Cornea*, 22 (4), 363-370.

Giguere, D., Olivie, G., Vidal, F., Toetsch, S., Girard, G., Ozaki, T., Kieffer, J.C., Nada, O., & Brunette, I. (2007). Laser ablation threshold dependence on pulse duration for fused silica and corneal tissues: experiments and modeling. *Journal of the Optical Society of America A*, 24 (6), 1562-1568.

Glezer, E.N., Milosavljevic, M., Huang, L., Finlay, R.J., Her, T.H., Callan, J.P., & Mazur, E. (1996). Three-dimensional optical storage inside transparent materials. Opt. Lett., 21, 2023-2025.

Han, M., Giese, G., Zickler, L., Sun, H., & Bille, J.F. (2004). Mini-invasive corneal surgery and imaging with femtosecond lasers. *Optics Express*, 12 (18), 4275-4281.

Holzer, M., Rabsilber, T., & Auffarth, G. (2006). Femtosecond laser-assisted corneal flap cuts: morphology, accuracy and histopathology. *Investigative Ophthalmology and Vision Science*, 47, 2828-2831.

Homoelle, D., Wielandy, S., Gaeta, A.L., Borrelli, N. F., & Smith, C. (1999). Infrared photosensitivity in silica glasses exposed to femtosecond laser pulses. Opt. Lett., 24, 1311-1313.

Hughes, A. (1977). The topography of vision in mammals of contrasting life style: comparative optics and retinal organization. In: *Handbook of Sensory Physiology*, V.II/5 (Berlin: Springer Verlag.

Huxlin, K.R., Ding, L., & Knox, W.H. (2008). Using a femtosecond laser to alter the refractive index of the cornea and lens. *ARVO* (Ft. Lauderdale, FL.

Hwang, D.J., Choi, T.Y., & Grigoropoulos, C.P. (2004). Liquid-assisted femtosecond laser drilling of straight and three-dimensional microchannels in glass. *App. Phys. A*, 79, 605-612.

Jester, J.V., Petroll, W.M., & Cavanagh, H.D. (1999). Corneal stromal wound healing in refractive surgery: the role of myofibroblasts. *Progress in Retinal & Eye Research*, 18 (3), 311-356.

Juhasz, T., Loesel, C., Horvath, C., Kurtz, R.M., & Mourou, G. (1999). Corneal refractive surgery with femtosecond lasers. *IEEE Journal of Quantum Electronics*, 5, 902-909.

Karigard, C.C.S., Sarkar, D.K., Jones, L.W., Moresoli, C., & Leung, K.T. (2004). Drying methods for XPS analysis of PureVision, Focus Night&Day and concentional hydrogel contact lens. *Applied Surface Science*, 230, 106-114.

Kim, J.Y., Kim, M.J., Kim, T.K., Choi, H., Pak, J.H., & Tchah, H. (2006). A femtosecond laser creates a stronger flap than a mechanical microkeratome. *Investigative Ophthalmology and Vision Science*, 47, 599-604.

König, K., Krauss, O., & Riemann, I. (2002). Intratissue surgery with 80MHz nanojoule femtosecond laser pulses in the near infrared. *Optics Express*, 10 (3), 171-176.

König, K., Riemann, I., Fischer, P., & Halbhuber, K. (1999). Intracellular nanosurgery with near infrared femtosecond laser pulses. *Cellular and Molecular Biology*, 45, 195-202.

König, K., Riemann, I., & Fritzsche, W. (2001). Nanodissection of human chromosomes with near-infrared femtosecond laser pulses. *Optics Letters*, 26 (11), 819-821.

Krueger, R.R., Trokel, S.L., & Schubert, H.D. (1985). Interaction of ultraviolet laser light with the cornea. *Investigative Ophthalmology and Vision Science*, 26, 1455-1464.

Kurtz, R.M., Horvath, C., Liu, H.H., Krueger, R.R., & Juhasz, T. (1998). Lamellar refractive surgery with scanned intrastromal picosecond and femtosecond laser pulses in animal eyes. *Journal of Refractive Surgery*, 14, 541-548.

Li, D.Y., & Borkman, R.F. (1990). Photodamage to calf lenses in vitro by excimer laser radiation at 308, 337, and 350 nm. *Investigative Ophthalmology and Visual Science*, 31 (10), 2180-2184.

Li, Y., Itoh, K., Watanabe, W., Yamada, K., Kuroda, D., Nishii, J., & Jiang, Y. (2001). Three-dimensional hole drilling of silica glass from the rear surface with femtosecond laser pulses. Opt. Lett., 26, 1912-1914.

Lim, T., Yang, S., Kim, M., & Tchah, H. (2006). Comparison of the intralase femtosecond laser and mechanical microkeratome for laser in situ keratomileusis. *American Journal of Ophthalmology*, 141, 833-839.

Loesel, F.H., Niemz, M.H., Bille, J.F., & Juhasz, T. (1996). Laser-induced optical breakdown on hard and soft tissue and its dependence on the pulse duration: experiment and model. *IEEE Journal of Quantum Electronics*, 32, 1717-1722.

Lubatschowski, H., Maatz, G., Heisterkamp, A., Hetzel, U., Drommer, W., Welling, H., & Ertmer, W. (2000). Application of ultrashort laser pulses for intrastromal refractive surgery. *Graefe's Archives of Clinical and Experimental Ophthalmology*, 238, 33-39.

Madeiros, F.W., Stapelton, W.M., Hammel, J., Krueger, R.R., Netto, M.V., & Wison, S.E. (2007). Wavefront analysis comparison of LASIK outcomes with the femtosecond laser and mechanical microkeratomes. *Journal of Refractive Surgery*, 23, 880-887.

Maruo, S., Nakamura, O., & Kawata, S. (1997). Three-dimentional microfabrication with two-photon-absorbed photopolymerization. *Opt. Lett.*, 22, 132-134.

Meek, K.M., Dennis, S., & Khan, S. (2003). Changes in the refractive index of the stroma and its extrafibrillar matrix when the cornea swells. *Biophysical Journal*, 85, 2205-2212.

Meltendorf, C., Burbach, G.J., Bühren, J., Bug, R., Ohrloff, C., & Deller, T. (2007). Corneal femtosecond laser keratotomy results in (56) References Cited

OTHER PUBLICATIONS isolated stromal injury and favorable wound-healing response. *Investigative Ophthalmology and Vision Science*, 48, 2068-2075.

Mendonca, C.R., Cerami, L.R., Shih, T., Tilghman, R.W., Baldacchini, T., & Mazur, E. (2008). Femtosecond laser waveguide micromachining of PMMA films with azoaromatic chromophores. *Opt. Express*, 16, 200-206.

Meschulach, D., Barad, Y., & Silberberg, Y. (2003). Measurement of ultrashort optical pulses by third-harmonic generation. *Journal of the Optical Society of America B*, 14, 2122-2125.

Minoshima, K., Kowalevicz, A.M., Hartl, I., Ippen, E.P., & Fujimoto, J.G. (2001). Photonic device fabrication in glass by use of nonlinear materials processing with a femtosecond laser oscillator. *Opt. Lett.*, 26, 1516-1518.

Netto, M.V., Mohan, R.R., Ambrosio, R., Jr., Hutcheon, A.E., Zieske, J.D., & Wilson, S.E. (2005). Wound healing in the cornea: a review of refractive surgery complications and new prospects for therapy. *Cornea*, 24 (5), 509-522.

Netto, M.V., Mohan, R.R., Medeiros, F.W., Dupps, W.J., Jr., Sinha, S., Krueger, R.R., Stapleton, W.M., Rayborn, M., Suto, C., & Wilson, S.E. (2007). Femtosecond laser and microkeratome corneal flaps: comparison of stromal wound healing and inflammation. *Journal of Refractive Surgery*, 23 (7), 667-676.

Pallikaris, I.G., & Saiganos, D.S. (1994). Excimer laser in situ keratomileusis and photorefractive keratectomy for correction of high myopia. *Journal of Refractive Surgery*, 10, 498-510.

Patel, S., Alio, J.L., & Perez-Santonja, J.J. (2004). Refractive index change in Bovine and human corneal stroma before and after LASIK: A study of untreated and re-treated corneas implicating stromal hydration. *Investigative Ophthalmology and Vision Science*, 45, 3523-3530.

Reichman, W.J., Krol, D.M., Shah, L., Yoshino, F., Arai, A., Eaton, S.M., & Herman, P.R. (2006). A spectroscopic comparison of femtosecond-laser-modified fused silica using kilohertz and megahertz laser systems. *J. of Appl. Phys.*, 99, 123112.

Schaffer, C.B., Garcia, J.F., & Mazur, E. (2003). Bulk heating of transparent materials using a high-repetition-rate femtosecond laser. *Applied Physics A*, 76, 351-354.

Schaffer, C.B., Brodeur, A., Garcia, J.F., & Mazur, E. (2001). Micromachining bulk glass by use of femtosecond laser pulses with nanojoule energy. *Opt. Lett.*, 26, 93-95.

Sowa, S., Watanabe, W., Tamaki, T., Nishii, J., & Itoh, K. (2006). Symmetric waveguides in poly(methyl methacrylate) fabricated by femtosecond laser pulses. *Opt. Express*, 14, 291-297.

Squier, J.A., Fittinghoff, D.N., Barty, C.P.J., Wilson, K.R., Muller, M., & Brakenhoff, G.J. (1998). Characterization of femtosecond pulses focused with high numerical aperture optics using interferometric surface-third-harmonic generation. *Optics Communications*, 147, 153-156.

Stern, D., Schoenlein, R.W., Puliafito, C.A., Dobi, E.T., Birngruber, R., & Fujimoto, J.G. (1989). Corneal ablation by nanosecond, picosecond, and femtosecond lasers at 532 and 625nm. *Archives of Ophthalmology*, 107, 587-592.

Stonecipher, K., Ignacio, T.S., & Stonecipher, M. (2006). Advances in refractive surgery: microkeratome and femtosecond laser flap creation in relation to safety, efficacy, predictability, and biomechanical stability. *Current Opinions in Ophthalmology*, 17, 368-37.

Streltsov, A.M., & Borrelli, N.F. (2001). Fabrication and analysis of a directional coupler written in glass by nanojoule femtosecond laser pulses. *Opt. Lett.*, 26, 42-43.

Stuart, B.C., Feit, M.D., Rubenchik, A.M., Shore, B.W., & Perry, M.D. (1995). Laser-induced damage in dielectrics with nanosecond to subpicosecond pulses. *Physical Review Letters*, 74, 2248-2251.

Talamo, J.H., Meltzer, J., & Gardner, J. (2006). Reproducibility of flap thickness with IntraLase FS and Moria LSK-1 and M2 microkeratomes. *Journal of Refractive Surgery*, 22, 556-561.

Tien, A.C., Backus, S., Kapteyn, H., Murnane, M., & Mourou, G. (1999). Short-pulse laser damage in transparent materials as a function of pulse duration. *Physical Review Letters*, 82, 3883-3886.

Tirlapur, U.K., & König, K. (2002a). Femtosecond near-infrared laser pulses as a versatile non-invasive tool for intra-tissue nanoprocessing in plants without compromising viability. *The Plant Journal*, 31(3), 365-374.

Tirlapur, U.K., & König, K. (2002b). Targeted transfection by femtosecond laser. *Nature*, 418, 290.

Touboul, D., Salin, F., Mortemousque, B., Chabassier, P., Mottay, E., Leger, F., & Colin, J. (2005). Advantages and disadvantages of the femtosecond laser microkeratome. *Journal Francais d'Ophthalmologie*, 28, 533-546.

Tran, D.B., Sarayba, M.A., Bor, Z., Garufis, C., Duh, Y.-J., Soltes, C.R., Juhasz, T., & Kurtz, R.M. (2005). Randomized prospective clinical study comparing induced aberrations with IntraLase and Hansatome flap creation in fellow eyes. Potential impact on wavefront guided laser in situ keratomileusis. *Journal of Cataract and Refractive Surgery*, 31 (1), 97-105.

Vogel, A., Capon, M.R., Asiyo-Vogel, M.N., & Birngruber, R. (1994). Intraocular photodisruption with picosecond and nanosecond laser pulses: tissue effects in cornea, lens, and retina *Investigative Ophthalmology and Visual Science*, 35 (7), 3032-3044.

Vogel, A., Linz, N., Freidank, S., & Paltauf, G. (2008). Femtosecond-laser-induced nanocavitation in water: implications for optical breakdown threshold and cell surgery. *Physical Review Letters*, 100, 038102-038101-038104.

Vogel, A., Noack, J., Huttman, G., & Paltauf, G. (2005). Mechanisms of femtosecond laser nanosurgery of cells and tissues. *Applied Physics B*, 81, 1015-1047.

Wilson, S.E. (2002). Analysis of the keratocyte apoptosis, keratocyte proliferation and myofibroblast transformation responses after photorefractive keratectomy and laser in situ keratomileusis. *Transactions of the American Ophthalmological Society*, 100, 411-433.

Witzgall, G., Vrigen, R., Yablonovitch, E., Doan, V., & Schwartz, B.J. (1998). Single-shot two-photon exposure of commercial photoresist for the production of three-dimensional structures. *Opt. Lett.*, 23, 1745-1747.

Zhou, G., Ventura, M.J., Vanner, M.R., & Gu, M. (2004). Use of ultrafast-laser-driven microexplosion for fabricating three-dimensional void-based diamond-lattice photonic crystals in a solid polymer material. *Opt. Lett.*, 29, 2240-2242.

Zoubir, A., Lopez, C., Richardson, M., & Richardson, K. (2004). Femtosecond laser fabrication of tubular waveguides in poly(methyl methacrylate). *Opt. Lett.*, 29, 1840-1842.

Ding, L., Huxlin, K.R., & Knox, W.H. (2007). Intrastromal refractive index change induced in cat corneas by femtosecond laser micromachining. *OSA Meeting—Frontiers in Optics* (San Jose, California.

Smith, W. (2000). Modern Optical Engineering. (McGraw-Hill Professional).

* cited by examiner

MULTI-PHOTON ABSORPTION FOR FEMTOSECOND MICROMACHINING AND REFRACTIVE INDEX MODIFICATION OF TISSUES

REFERENCE TO RELATED APPLICATIONS

The present application is a continuation-in-part of U.S. patent application Ser. No. 12/146,976, filed Jun. 26, 2008, currently pending, which claims the benefit of U.S. Provisional Patent Application Nos. 60/929,397, filed Jun. 26, 2007, and 61/026,890, filed Feb. 7, 2008. The disclosures of all of those applications are hereby incorporated by reference in their entireties into the present application.

STATEMENT OF GOVERNMENT INTEREST

The work leading to the present invention was supported in part by NIH Grant Nos. R01 EY015836 and 08P0EY01319F. The government has certain rights in the invention.

CREATE ACT STATEMENT

The claimed invention was made by, on behalf of, or in connection with one or more of the following parties to a joint university-corporation research agreement: The University of Rochester, and Bausch & Lomb, Inc. The agreement was in effect on and before the date the claimed invention was made, and the claimed invention was made as a result of activities undertaken within the scope of the agreement.

FIELD OF THE INVENTION

The present invention is directed to vision correction and more particularly to vision correction by modifying the index of refraction of ocular tissue in the eye by a high-repetition, low-pulse energy femtosecond laser and two-photon absorption or other multi-photon absorption.

DESCRIPTION OF RELATED ART

Conventional ultraviolet nanosecond excimer lasers have been successfully used for corneal refractive surgery, including photorefractive keratectomy (PRK), laser-assisted in situ keratomileusis (LASIK) and laser sub-epithelial keratomileusis (LASEK). By ablating corneal tissue through direct absorption of ultraviolet light, these lasers alter the curvature, thickness and ultimately, the optical power of the cornea (Krueger, Trokel & Schubert, 1985, Pallikaris & Saiganos, 1994).

The rapid development of femtosecond laser technology has provided an additional tool for corneal refractive surgery. In contrast to the ultraviolet lasers, femtosecond laser pulses in the near infrared can pass through transparent corneal tissue without significant one-photon absorption. Only when pulses are focused inside the cornea, is the intensity of the beam sufficient to cause nonlinear, typically multi-photon absorption, and a range of modifications to the tissue. Because the absorption is strongly nonlinear, the laser-affected region tends to be very small, leaving the surrounding region unaffected, or minimally affected (Giguere, Olivie, Vidal, Toetsch, Girard, Ozaki, Kieffer, Nada & Brunette, 2007, Loesel, Niemz, Bille & Juhasz, 1996, Vogel, Noack, Huffman & Paltauf, 2005). This unique capability for high-precision micromachining at different depths of the material is the primary reason for the introduction of femtosecond lasers to refractive surgery, where their main application has been in corneal flap cutting (Han, Giese, Zickler, Sun & Bille, 2004, Holzer, Rabsilber & Auffarth, 2006, Juhasz, Loesel, Horvath, Kurtz & Mourou, 1999, Kim, Kim, Kim, Choi, Pak & Tchah, 2006, Kurtz, Horvath, Liu, Krueger & Juhasz, 1998, Lubatschowski, Maatz, Heisterkamp, Hetzel, Drommer, Welling & Ertmer, 2000, Meltendorf, Burbach, Buhren, Bug, Ohrloff & Deller, 2007). For this application, femtosecond laser pulses with a low repetition rate (Hz-kHz range) are used to induce photo-disruption and destructive, optical breakdown of a single layer within the corneal stroma. This is generally associated with high-density microplasma generation, bubble formation and shock-wave emission, often extending beyond the focal region. Compared with mechanical blade microkeratomes, femtosecond lasers are better able to define the depth of the cut, eliminating some flap-related complications and generally improving visual outcomes (Lim, Yang, Kim & Tchah, 2006, Madeiros, Stapelton, Hammel, Krueger, Netto & Wison, 2007, Talamo, Meltzer & Gardner, 2006, Touboul, Salin, Mortemousque, Chabassier, Mottay, Leger & Colin, 2005). However, femtosecond laser flaps are more variable in thickness than intended, like any cut, they cause biomechanical changes in the cornea, and since tissue is destroyed, a wound healing reaction ensues (Stonecipher, Ignacio & Stonecipher, 2006, Talamo et al., 2006, Tran, Sarayba, Bor, Garufis, Duh, Soltes, Juhasz & Kurtz, 2005). This wound healing reaction includes the differentiation of the usually quiescent and supportive stromal keratocytes into reactive, inflammatory and contractile myofibroblasts (Jester, Petroll & Cavanagh, 1999, Wilson, 2002). Myofibroblasts appear responsible for most of the negative side-effects of laser refractive surgery, including haze or loss of corneal transparency, and unintended changes in corneal shape, which negatively impact the optical quality of the eye (Jester et al., 1999, Netto, Mohan, Ambrosio, Hutcheon, Zieske & Wilson, 2005). While increasingly popular, femtosecond laser flap cutting remains limited by its high cost, accessibility, as well as uncertainty about its long-term photochemical, mechanical and biological effects (Netto, Mohan, Medeiros, Dupps, Sinha, Krueger, Stapleton, Rayborn, Suto & Wilson, 2007, Stonecipher et al., 2006). Recent reports have detailed negative side-effects of this technique, particularly in terms of tissue destruction, which, at some laser settings, appears stronger than following mechanical microkeratome cuts (Netto et al., 2007, Stonecipher et al., 2006).

The ability to alter corneal shape or optics without causing tissue destruction (and thus, a wound healing response) would significantly decrease or eliminate the negative side effects that compromise optical outcomes and ocular health following corneal manipulations. However, most clinical femtosecond lasers currently employ μJ or mJ pulses with a low-repetition-rate (Hz-kHz range) and spot diameters in the range of several μm (Juhasz et al., 1999, Kurtz et al., 1998). In clear ocular tissues such as the cornea, even several-nJ femtosecond laser pulses with 170 fs pulse duration and 80 MHz repetition rate have only been reported to induce destructive optical breakdown (König, Krauss & Riemann, 2002). For such lasers, the diffusion time of non-linearly-absorbed laser energy is longer than the time interval between laser pulses. As a result, absorbed energy accumulates locally, with destructive consequences (Schaff, Garcia & Mazur, 2003).

This contrasts with femtosecond laser parameters that have been established for some other applications. It was these applications that first suggested to us that it might be possible to use femtosecond lasers to do things other than pulverize biological materials. High-repetition-rate (>1 MHz) femtosecond laser oscillators with pulse energies on the order of nJ have successfully been used to create structures in different transparent optical materials, a process we will refer to as "micromachining" in this application.

Micromachining has been successfully performed in various silica glasses (Davis, Miura, Sugimoto & Hirao, 1996, Eaton, Zhang, Herman, Yoshino, Shah, Bovatsek & Arai, 2005b, Glezer, Milosavljevic, Huang, Finlay, Her, Callan & Mazur, 1996, Homoelle, Wielandy, Gaeta, Borrelli & Smith, 1999, Hwang, Choi & Grigoropoulos, 2004, Li, Itoh, Watanabe, Yamada, Kuroda, Nishii & Jiang, 2001, Minoshima, Kowalevicz, Hartl, Ippen & Fujimoto, 2001, Schaffer, Brodeur, Garcia & Mazur, 2001, Streltsov & Borrelli, 2001) and photoresisted polymers (Day & Gu, 2005, Ding, Blackwell, Künzler & Knox, 2006, Maruo, Nakamura & Kawata, 1997, Mendonca, Cerami, Shih, Tilghman, Baldacchini & Mazur, 2008, Sowa, Watanabe, Tamaki, Nishii & Itoh, 2006, Witzgall, Vrigen, Yablonovitch, Doan & Schwartz, 1998, Zhou, Ventura, Vanner & Gu, 2004, Zoubir, Lopez, Richardson & Richardson, 2004). Compared with the linear absorption induced by conventional continuous wave, nanosecond, and picosecond lasers, during micromachining, femtosecond laser pulses are tightly focused inside of transparent materials through a high (or medium) numerical aperture objective. The energy transfer rate achieved in the induced non-linear absorption is higher than the rate in which it can be dissipated into the surrounding lattice, allows a localized but non-destructive energy deposition in the focal volume. The nonlinear absorption will usually create a microplasma that is responsible for the observed material modifications, but which leaves the surrounding medium unaffected. Examples of structures created using femtosecond laser micromachining include optical waveguides and couplers (Davis et al., 1996, Eaton et al., 2005b, Homoelle et al., 1999, Mendonca et al., 2008, Minoshima et al., 2001, Schaffer et al., 2001, Streltsov & Borrelli, 2001, Zoubir et al., 2004), 3D storages (Glezer et al., 1996), optical gratings (Ding et al., 2006), photonic crystals (Zhou et al., 2004) and microfluidic channels (Day & Gu, 2005, Hwang et al., 2004, Li et al., 2001). In both silicone and non-silicone-based hydrogels, our group has shown that femtosecond micromachining works by inducing a significant change in refractive index of the materials without visible plasma luminescence or bubble formation, and without the generation of undesirable scattering or absorbing centers (Ding et al., 2006).

One of the most exciting uses of femtosecond lasers in biology was developed relatively recently and was instrumental in suggesting that femtosecond micromachining settings could be used non-destructively in living biological tissues. The research groups of Karsten König and Alfred Vogel, both in Germany, have demonstrated that it is possible to perform nanosurgery in living cells with near-infrared femtosecond lasers (König et al., 2002, König, Riemann, Fischer & Halbhuber, 1999, König, Riemann & Fritzsche, 2001, Tirlapur & König, 2002a, Tirlapur & König, 2002b, Vogel, Linz, Freidank & Paltauf, 2008, Vogel et al., 2005). While most femtosecond laser nanosurgeries involve (by definition) some sort of disruption, either affecting membranes, organelles or other cellular components, they can be performed with such precision and selectivity so as not to kill the cells (Tirlapur & König, 2002a, Tirlapur & König, 2002b, Vogel et al., 2005). This critical finding was a strong indication that femtosecond laser pulse energy, repetition rate and pulse duration could all be manipulated to generate tissue changes on a scale that could range from cellular nanosurgery to laser refractive surgery, but with less destruction than currently attained. This prompted us to perform the experiments that led to the development of IRIS, as disclosed in the above-cited parent application.

By adapting femtosecond micromachining approaches developed in hydrogels (Ding et al., 2006), our group was the first to perform Intra-tissue Refractive Index Shaping (IRIS) in biological tissues. To do this, we first measured the optical breakdown thresholds of lightly-fixed cat corneas and lenses. We then reduced femtosecond laser pulse energies below these optical breakdown thresholds to create grating patterns that are associated with a change in the refractive index of the tissue. Some of these results have been written up and currently in press at IOVS (Ding, Knox, Bühren, Nagy & Huxlin, 2008).

Choosing the right laser parameters is critical for achieving IRIS in biological tissues. Not only does the femtosecond laser fluence at the objective focus have to be below the optical breakdown threshold of the tissue, it also had to be strong enough to induce some nonlinear changes, and the scan speed must be set within a specified range. In the past two decades, extensive experimental and theoretical work has been done to characterize laser-induced optical breakdown thresholds in different materials, including the cornea (Docchio, Sacchi & Marshall, 1986, Du, Liu, Korn, Squier & Mourou, 1994, Giguere et al., 2007, Loesel et al., 1996, Stern, Schoenlein, Puliafito, Dobi, Birngruber & Fujimoto, 1989, Stuart, Feit, Rubenchik, Shore & Perry, 1995, Tien, Backus, Kapteyn, Murnane & Mourou, 1999, Vogel et al., 2005) and the lens (Brazitikos, D'Amico, Bochow, Hmelar, Marcellino & Stangos, 1998, Li & Borkman, 1990, Vogel, Capon, Asiyo-Vogel & Birngruber, 1994). However, most of this work centered on the use of continuous wave (CW) lasers or on single pulses from low-repetition-rate lasers in which thermal diffusion time is much shorter than the time interval between adjacent pulses. Thus, each pulse is responsible for a change in the material. Indeed, it has been established that for pulses longer than 10 ps, the optical breakdown threshold fluence scales as the square root of the pulse duration (Du et al., 1994). For pulses shorter than 10 ps but longer than about 100 fs (which is the case with IRIS settings), the experimental results show a departure from this dependence. However, whether threshold fluence increases or decreases as pulse durations get shorter remains a challenging question (Stern et al., 1989, Stuart et al., 1995, Tien et al., 1999). Some models predict that the threshold would first increase, then decrease when pulse duration becomes shorter than 100 fs, but there is no solid experimental evidence to support this (Tien et al., 1999). More recently, it has been claimed that for corneal stroma, the breakdown threshold is almost plateau-like when the pulse duration is between 100 fs and 1 ps, with a rapid decrease in threshold for pulse durations in the low end of the femtosecond range (Giguere et al., 2007). However, insufficient experimentation on cornea and lens using sub-100 fs pulses makes it difficult to support this prediction and furthermore, existing data were collected using single pulses from low-repetition-rate lasers.

When high-repetition-rate femtosecond laser pulses are used, cumulative, free-electron-mediated chemical effects, photochemical bond breaking and thermal effects contribute to the laser-tissue interaction. As a result, the breakdown threshold fluence may be quite different from that predicted by current models (Vogel et al., 2005). Several studies on the effects of high-repetition-rate femtosecond lasers on fused silica and borosilicate glass have found that laser pulses greatly increased the temperature of the materials at the laser focus (Eaton, Zhang, Herman, Yoshino, Shah, Bovatsek & Arai, 2005a). Vogel calculated the temperature change in water would be >10° K. with a 0.6 NA focusing lens and 100 fs laser pulses (Vogel et al., 2005), assuming that with each pulse, an energy density of 1 J/cm$^3$ at the center of the initial temperature distribution is deposited. Using very high-repetition-rate (93 MHz), ultra-short laser pulses (27 fs), we found the optical breakdown threshold for the 0.70 NA focusing condition in lightly-fixed corneal stroma and lens cortex to be 55 mW and 75 mW average laser power respectively (Ding et al., 2008). This corresponds to 0.6 nJ and 0.8 nJ pulse energies respectively, both lower than the optical breakdown power reported by König and colleagues using 1 nJ pulse energy, 170 fs pulse duration and 1.30 NA focusing in porcine corneas (König et al., 2002). By using 30 mW and 45 mW average laser power (0.3 nJ and 0.5 nJ pulses), we were able to induce IRIS, without accompanying photo-disruption and tissue destruction.

Our preliminary experiments demonstrated, for the first time, that it is possible to cause low-scattering-loss, refractive index modifications in lightly-fixed cat cornea and lens using 93 MHz repetition rate, 27 fs laser pulses with 0.3 nJ and 0.5 nJ pulse energies. These modifications were visible only using DIC microscopy and were not associated with apparent tissue damage. They represent refractive index changes between 0.005±0.001 and 0.021±0.001. Preservation of IRIS over a month of refrigerated storage suggested that the femtosecond laser-induced modifications were likely to involve relatively long-term molecular/structural alterations. In related experiments involving silicone hydrogels, the micromachined gratings (and associated Raman spectra) were observed to persist for up to one year, even after drying and rehydration of the hydrogel (Ding, Cancado, Novotny, Knox, Anderson, Jani, Blackwell, Künzler & Smith, in preparation).

Although the refractive index changes induced in cornea and lens tissue to date have been relatively small, their impact on optical power is still significant. Based on published values for the power (39D) and native refractive index (1.376) of the cat cornea (Hughes, 1977), IRIS should generate a change in corneal power ranging between 0.14D and 0.56D (assuming an index change between 0.005 and 0.02). Similarly, for the cat lens (power=53D, refractive index of the homogeneous lens=1.554) (Hughes, 1977), the refractive index changes induced by micromachining should theoretically alter lenticular power by between 0.5D and 0.7D.

However, even further improvement is possible.

Citations in the present disclosure are to the following references, which are hereby incorporated by reference in their entireties into the present disclosure:

Born, M., & Wolf, E. (1970). Principle of Optics. (Pergamon Press, Oxford.

Brazitikos, P. D., D'Amico, D. J., Bochow, T. W., Hmelar, M., Marcellino, G. R., & Stangos, N. T. (1998). Experimental Ocular Surgery with a High-Repetition-Rate Erbium: YAG Laser. *Investigative Ophthalmology and Visual Science,* 39 (9), 1667-1675.

Davis, K. M., Miura, K., Sugimoto, N., & Hirao, K. (1996). Writing waveguides in glass with a femtosecond laser. *Opt. Lett.,* 21, 1729-1731.

Day, D., & Gu, M. (2005). Microchannel fabrication in PMMA based on localized heating by nanojoule high repetition rate femtosecond pulses. *Opt. Express,* 13, 5939-5946.

Ding, L., Blackwell, R., Künzler, J. F., & Knox, W. H. (2006). Large refractive index change in silicone-based and non-silicone-based hydrogel polymers induced by femtosecond laser micro-machining. *Optics Express,* 14 (24), 11901-11909.

Ding, L., Cancado, L. G., Novotny, L., Knox, W. H., Anderson, N., Jani, D., Blackwell, R. I., Künzler, J. F., & Smith, T. (in preparation). Micro-Raman spectroscopic study of silicone-based hydrogel polymers modified by megahertz femtosecond laser pulses.

Ding, L., Huxlin, K. R., & Knox, W. H. (2007). Intrastromal refractive index change induced in cat corneas by femtosecond laser micromachining. *OSA Meeting—Frontiers in Optics* (San Jose, Calif.

Ding, L., Knox, W. H., Bühren, J., Nagy, L. J., & Huxlin, K. R. (2008). Intra-tissue Refractive Index Shaping (IRIS) of the cornea and lens using a low-pulse-energy femtosecond laser oscillator. *Investigative Ophthalmolgy and Visual Science,* in press Docchio, F., Sacchi, C. A., & Marshall, J. (1986). Experimental investigation of optical breakdown thresholds in ocular media under single pulse irradiation with different pulse durations. *Lasers Ophthalmol,* 1, 83-93.

Du, D., Liu, X., Korn, G., Squier, J. A., & Mourou, G. (1994). Laser induced breakdown by impact ionization in SiO2 with pulse widths from 7 ns to 150 fs. *Applied Physics Letters,* 64, 3071-3073.

Eaton, S. M., Zhang, H., Herman, P. R., Yoshino, F., Shah, L., Bovatsek, J., & Arai, A. Y. (2005a). Heat accumulation effects in femtosecond laser-written waveguides with variable repetition rate. *Optics Express,* 13, 4708-4716.

Eaton, S. M., Zhang, H., Herman, P. R., Yoshino, F., Shah, L., Bovatsek, J., & Arai, A. Y. (2005b). Heat accumulation effects in femtosecond laser-written waveguides with variable repetition rate. *Opt. Express,* 13, 4708-4716.

Fisher, B. T., Masiello, K. A., Goldstein, M. H., & Hahn, D. W. (2003). Assessment of transient changes in corneal hydration using confocal Raman spectroscopy. *Cornea,* 22 (4), 363-370.

Giguere, D., Olivie, G., Vidal, F., Toetsch, S., Girard, G., Ozaki, T., Kieffer, J. C., Nada, O., & Brunette, I. (2007). Laser ablation threshold dependence on pulse duration for fused silica and corneal tissues: experiments and modeling. *Journal of the Optical Society of America A,* 24 (6), 1562-1568.

Glezer, E. N., Milosavljevic, M., Huang, L., Finlay, R. J., Her, T. H., Callan, J. P., & Mazur, E. (1996). Three-dimensional optical storage inside transparent materials. *Opt. Lett.,* 21, 2023-2025.

Han, M., Giese, G., Zickler, L., Sun, H., & Bille, J. F. (2004). Mini-invasive corneal surgery and imaging with femtosecond lasers. *Optics Express,* 12 (18), 4275-4281.

Holzer, M., Rabsilber, T., & Auffarth, G. (2006). Femtosecond laser-assisted corneal flap cuts: morphology, accuracy and histopathology. *Investigative Ophthalmology and Vision Science,* 47, 2828-2831.

Homoelle, D., Wielandy, S., Gaeta, A. L., Borrelli, N. F., & Smith, C. (1999). Infrared photosensitivity in silica glasses exposed to femtosecond laser pulses. *Opt. Lett.,* 24, 1311-1313.

Hughes, A. (1977). The topography. of vision in mammals of contrasting life style: comparative optics and retinal organization. In: *Handbook of Sensory Physiology, V.IV/5* (Berlin: Springer Verlag.

Huxlin, K. R., Ding, L., & Knox, W. H. (2008). Using a femtosecond laser to alter the refractive index of the cornea and lens. *ARVO* (Ft. Lauderdale, Fla.

Hwang, D. J., Choi, T. Y., & Grigoropoulos, C. P. (2004). Liquid-assisted femtosecond laser drilling of straight and three-dimensional microchannels in glass. *App. Phys. A*, 79, 605-612.

Jester, J. V., Petroll, W. M., & Cavanagh, H. D. (1999). Corneal stromal wound healing in refractive surgery: the role of myofibroblasts. *Progress in Retinal & Eye Research*, 18 (3), 311-356.

Juhasz, T., Loesel, C., Horvath, C., Kurtz, R. M., & Mourou, G. (1999). Corneal refractive surgery with femtosecond lasers. *IEEE Journal of Quantum Electronics*, 5, 902-909.

Karlgard, C. C. S., Sarkar, D. K., Jones, L. W., Moresoli, C., & Leung, K. T. (2004). Drying methods for XPS analysis of PureVision, Focus Night&Day and concentional hydrogel contact lens. *Applied Surface Science*, 230, 106-114.

Kim, J. Y., Kim, M. J., Kim, T. K., Choi, H., Pak, J. H., & Tchah, H. (2006). A femtosecond laser creates a stronger flap than a mechanical microkeratome. *Investigative Ophthalmology and Vision Science*, 47, 599-604.

König, K., Krauss, O., & Riemann, I. (2002). Intratissue surgery with 80 MHz nanojoule femtosecond laser pulses in the near infrared. *Optics Express*, 10 (3), 171-176.

König, K., Rieman, I., Fischer, P., & Halbhuber, K. (1999). Intracellular nanosurgery with near infrared femtosecond laser pulses. *Cellular and Molecular Biology*, 45, 195-202.

König, K., Riemann, I., & Fritzsche, W. (2001). Nanodissection of human chromosomes with near-infrared femtosecond laser pulses. *Optics Letters*, 26 (11), 819-821.

Krueger, R. R., Trokel, S. L., & Schubert, H. D. (1985). Interaction of ultraviolet laser light with the cornea. *Investigative Ophthalmology and Vision Science*, 26, 1455-1464.

Kurtz, R. M., Horvath, C., Liu, H. H., Krueger, R. R., & Juhasz, T. (1998). Lamellar refractive surgery with scanned intrastromal picosecond and femtosecond laser pulses in animal eyes. *Journal of Refractive Surgery*, 14, 541-548.

Li, D. Y., & Borkman, R. F. (1990). Photodamage to calf lenses in vitro by excimer laser radiation at 308, 337, and 350 nm. *Investigative Ophthalmology and Visual Science*, 31 (10), 2180-2184.

Li, Y., Itoh, K., Watanabe, W., Yamada, K., Kuroda, D., Nishii, J., & Jiang, Y. (2001). Three-dimensional hole drilling of silica glass from the rear surface with femtosecond laser pulses. *Opt. Lett.*, 26, 1912-1914.

Lim, T., Yang, S., Kim, M., & Tchah, H. (2006). Comparison of the intralase femtosecond laser and mechanical microkeratome for laser in situ keratomileusis. *American Journal of Ophthalmology*, 141, 833-839.

Loesel, F. H., Niemz, M. H., Bille, J. F., & Juhasz, T. (1996). Laser-induced optical breakdown on hard and soft tissue and its dependence on the pulse duration: experiment and model. *IEEE Journal of Quantum Electronics*, 32, 1717-1722.

Lubatschowski, H., Maatz, G., Heisterkamp, A., Hetzel, U., Drommer, W., Welling, H., & Ertmer, W. (2000). Application of ultrafast laser pulses for intrastromal refractive surgery. *Graefe's Archives of Clinical and Experimental Ophthalmology*, 238, 33-39.

Madeiros, F. W., Stapelton, W. M., Hammel, J., Krueger, R. R., Netto, M. V., & Wison, S. E. (2007). Wavefront analysis comparison of LASIK outcomes with the femtosecond laser and mechanical microkeratomes. *Journal of Refractive Surgery*, 23, 880-887.

Maruo, S., Nakamura, O., & Kawata, S. (1997). Three-dimensional microfabrication with two-photon-absorbed photopolymerization. *Opt. Lett.*, 22, 132-134.

Meek, K. M., Dennis, S., & Khan, S. (2003). Changes in the refractive index of the stroma and its extrafibrillar matrix when the cornea swells. *Biophysical Journal*, 85, 2205-2212.

Meltendorf, C., Burbach, G. J., Bühren, J., Bug, R., Ohrloff, C., & Deller, T. (2007). Corneal femtosecond laser keratotomy results in isolated stromal injury and favorable wound-healing response. *Investigative Ophthalmology and Vision Science*, 48, 2068-2075.

Mendonca, C. R., Cerami, L. R., Shih, T., Tilghman, R. W., Baldacchini, T., & Mazur, E. (2008). Femtosecond laser waveguide micromachining of PMMA films with azoaromatic chromophores. *Opt. Express*. 16, 200-206.

Meschulach, D., Barad, Y., & Silberberg, Y. (2003). Measurement of ultrashort optical pulses by third-harmonic generation. *Journal of the Optical Society of America B*, 14, 2122-2125.

Minoshima, K., Kowalevicz, A. M., Hartl, I., Ippen, E. P., & Fujimoto, J. G. (2001). Photonic device fabrication in glass by use of nonlinear materials processing with a femtosecond laser oscillator. *Opt. Lett.*, 26, 1516-1518.

Netto, M. V., Mohan, R. R., Ambrosio, R., Jr., Hutcheon, A. E., Zieske, J. D., & Wilson, S. E. (2005). Wound healing in the cornea: a review of refractive surgery complications and new prospects for therapy. *Cornea*, 24 (5), 509-522.

Netto, M. V., Mohan, R. R., Medeiros, F. W., Dupps, W. J., Jr., Sinha, S., Krueger, R. R., Stapleton, W. M., Rayborn, M., Suto, C., & Wilson, S. E. (2007). Femtosecond laser and microkeratome corneal flaps: comparison of stromal wound healing and inflammation. *Journal of Refractive Surgery*, 23 (7), 667-676.

Pallikaris, I. G., & Saiganos, D. S. (1994). Excimer laser in situ keratomileusis and photorefractive keratectomy for correction of high myopia. *Journal of Refractive Surgery*, 10, 498-510.

Patel, S., Alio, J. L., & Perez-Santonja, J. J. (2004). Refractive index change in Bovine and human corneal stroma before and after LASIK: A study of untreated and retreated corneas implicating stromal hydration. *Investigative Ophthalmology and Vision Science*, 45, 3523-3530.

Reichman, W. J., Krol, D. M., Shah, L., Yoshino, F., Arai, A., Eaton, S. M., & Herman, P. R. (2006). A spectroscopic comparison of femtosecond-laser-modified fused silica using kilohertz and megahertz laser systems. *J. of Appl. Phys.*, 99, 123112.

Schaff, C. B., Garcia, J. F., & Mazur, E. (2003). Bulk. heating of transparent materials using a high-repetition-rate femtosecond laser. *Applied Physics A*, 76, 351-354.

Schaffer, C. B., Brodeur, A., Garcia, J. F., & Mazur, E. (2001). Micromachining bulk glass by use of femtosecond laser pulses with nanojoule energy. *Opt. Lett.*, 26, 93-95.

Smith, W. (2000). *Modern Optical Engineering.* (McGraw-Hill Professional).

Sowa, S., Watanabe, W., Tamaki, T., Nishii, J., & Itoh, K. (2006). Symmetric waveguides in poly(methyl methacrylate) fabricated by femtosecond laser pulses. *Opt. Express*, 14, 291-297.

Squier, J. A., Fittinghoff, D. N., Barty, C. P. J., Wilson, K. R., Muller, M., & Brakenhoff, G. J. (1998). Characterization of femtosecond pulses focused with high numerical aperture optics using interferometric surface-third-harmonic generation. *Optics Communications*, 147, 153-156.

Stern, D., Schoenlein, R. W., Puliafito, C. A., Dobi, E. T., Birngruber, R., & Fujimoto, J. G. (1989). Corneal ablation by nanosecond, picosecond, and femtosecond lasers at 532 and 625 nm. *Archives of Ophthalmology*, 107, 587-592.

Stonecipher, K., Ignacio, T. S., & Stonecipher, M. (2006). Advances in refractive surgery: microkeratome and femtosecond laser flap creation in relation to safety, efficacy, predictability, and biomechanical stability. *Current Opinions in Ophthalmology*, 17, 368-372.

Streltsov, A. M., & Borrelli, N. F. (2001). Fabrication and analysis of a directional coupler written in glass by nanojoule femtosecond laser pulses. *Opt. Lett.*, 26, 42-43.

Stuart, B. C., Feit, M. D., Rubenchik, A. M., Shore, B. W., & Perry, M. D. (1995). Laser-induced damage in dielectrics with nanosecond to subpicosecond pulses. *Physical Review Letters*, 74, 2248-2251.

Talamo, J. H., Meltzer, J., & Gardner, J. (2006). Reproducibility of flap thickness with IntraLase FS and Moria LSK-1 and M2 microkeratomes. *Journal of Refractive Surgery*, 22, 556-561.

Tien, A. C., Backus, S., Kapteyn, H., Murnane, M., & Mourou, G. (1999). Short-pulse laser damage in transparent materials as a function of pulse duration. *Physical Review Letters*, 82, 3883-3886.

Tirlapur, U. K., & König, K. (2002a). Femtosecond near-infrared laser pulses as a versatile non-invasive tool for intra-tissue nanoprocessing in plants without compromising viability. *The Plant Journal*, 31 (3), 365-374.

Tirlapur, U. K., & König, K. (2002b). Targeted transfection by femtosecond laser. *Nature*, 418, 290.

Touboul, D., Salin, F., Mortemousque, B., Chabassier, P., Mottay, E., Leger, F., & Colin, J. (2005). Advantages and disadvantages of the femtosecond laser microkeratome. *Journal Francais d'Ophthalmologie*, 28, 533-546.

Tran, D. B., Sarayba, M. A., Bor, Z., Garufis, C., Duh, Y.-J., Soltes, C. R., Juhasz, T., & Kurtz, R. M. (2005). Randomized prospective clinical study comparing induced aberrations with IntraLase and Hansatome flap creation in fellow eyes. Potential impact on wavefront guided laser in situ keratomileusis. *Journal of Cataract and Refractive Surgery*, 31 (1), 97-105.

Vogel, A., Capon, M. R., Asiyo-Vogel, M. N., & Birngruber, R. (1994). Intraocular photodisruption with picosecond and nanosecond laser pulses: tissue effects in cornea, lens, and retina *Investigative Ophthalmology and Visual Science*, 35 (7), 3032-3044.

Vogel, A., Linz, N., Freidank, S., & Paltauf, G. (2008). Femtosecond-laser-induced nanocavitation in water: implications for optical breakdown threshold and cell surgery. *Physical Review Letters*, 100, 038102-038101-038104.

Vogel, A., Noack, J., Huttman, G., & Paltauf, G. (2005). Mechanisms of femtosecond laser nanosurgery of cells and tissues. *Applied Physics B*, 81, 1015-1047.

Wilson, S. E. (2002). Analysis of the keratocyte apoptosis, keratocyte proliferation and myofibroblast transformation responses after photorefractive keratectomy and laser in situ keratomileusis. *Transactions of the American Ophthalmological Society*, 100, 411-433.

Witzgall, G., Vrigen, R., Yablonovitch, E., Doan, V., & Schwartz, B. J. (1998). Single-shot two-photon exposure of commercial photoresist for the production of three-dimensional structures. *Opt. Lett.*, 23, 1745-1747.

Zhou, G., Ventura, M. J., Vanner, M. R., & Gu, M. (2004). Use of ultrafast-laser-driven microexplosion for fabricating three-dimensional void-based diamond-lattice photonic crystals in a solid polymer material. *Opt. Lett.*, 29, 2240-2242.

Zoubir, A., Lopez, C., Richardson, M., & Richardson, K. (2004). Femtosecond laser fabrication of tubular waveguides in poly(methyl methacrylate). *Opt. Lett.*, 29, 1840-1842.

SUMMARY OF THE INVENTION

It is therefore an object of the invention to implement such an improvement.

It is a further object of the invention to implement such an improvement using two-photon absorption (TPA) or, more generally, multi-photon absorption.

More recent experiments using a process to chemically enhance the two-photon absorption properties of both tissues resulted in at least a doubling of the refractive index changes and a several hundred fold increase in the micromachining speeds attained. The manipulations we have described could potentially be applied to multiple other biological tissues. However, our wealth of expertise and data with respect to corneal and lens properties make ocular tissues the ideal system for a first-pass investigation of IRIS in living tissues.

Ongoing experiments in our laboratories are generating information about the cellular and molecular mechanisms underlying IRIS in the living cornea, and allowing us to gain critical knowledge that can be used to further manipulate the size, placement and design of micromachined patterns, as well as the magnitude of the refractive index changes with which they are associated. The ability to alter the native refractive index of the cornea and lens without causing significant tissue damage has important theoretical and practical implications. By understanding how laser power can be used to alter tissues non-destructively, and by understanding the nature of these alterations, we could open up an entirely new branch in the field of laser biology. Among other things, this could completely change our approach to laser refractive surgery, and to vision correction more generally. For instance, the preservation of tissue clarity during the treatment allows the application of IRIS for the creation of corneal fiducial markings that could be used to align eye trackers during LASIK, and for refractive corrections in a closed-loop approach, e.g. with specific benefit for the correction of higher-order aberrations, as well as for "touch-up corrections" of ocular surface defects. More broadly, the feasibility of IRIS in living tissues would offer new possibilities for non-invasive alterations, marking or pattern-inscription within living organisms. From a theoretical stand-point, it also provides a unique opportunity to better understand and define the extent to which we can optically manipulate even large areas of living tissues without inducing a significant wound healing reaction.

The inventors have found that various ranges of parameters are particularly useful in implementing the present invention. In treatment of the eye, the laser wavelength should be such that the tissues through which laser pulses pass are transparent to the pulses. There should also be no damage to the retina; any change should be confined to the tissue located at the spot of focus of the pulses. Also, for non-destructive alteration of ocular tissue, a $CO_2$ laser or excimer laser should not be used, since there should be no ablation or removal of the tissue.

A laser pulse frequency (repetition rate) of 93 MHz is useful for many applications. A preferable range is from 1 MHz to 10 GHz, and more preferably from 10 to 500 MHz.

Linked to the pulse frequency is the average power. A preferable range is from 1 to 1,000 mW, and more preferably 10 to 100 mW, and more preferably still from 50 to 60 mW. The energy of each pulse should preferably be less than 1 nJ and more preferably less than 0.5 nJ, although a range from 0.01 to 10 nJ and more preferably from 0.1 to 2 nJ can be used.

A laser pulse width of 30 fs is useful for many applications. A preferable range is from 5 fs to 1 ps, and more preferably from 10 to 100 fs.

The scanning speed of the laser is preferably 0.4 µm/s, although, depending on the equipment, ranges such as 0.1 µm/s to 10 mm/s can be implemented.

The wavelength should, as noted above, be one to which the tissues through which the laser pulses must pass are transparent. It should also preferably be just barely within the visible range for the patient, or outside of the visible range (e.g., near-infrared), so as not to bother the patient. A wavelength of 800 nm is useful; preferable ranges include 600-1,000 nm (and more preferably 700-900 nm) and above 1,000 nm.

The laser pulses are focused to a spot size that is preferably 1 µm. Preferable ranges include 0.5 µm to 2, 10, or 50 µm.

Various structures can be produced in the ocular tissue. Examples include high refractive index structures such as Bragg gratings, microlens arrays, optical zone plates, and Fresnel lenses.

BRIEF DESCRIPTION OF THE DRAWINGS

A preferred embodiment of the present invention will be set forth in detail with reference to the drawings, in which.

DETAILED DESCRIPTION OF THE PREFERRED EMBODIMENT

A preferred embodiment of the present invention will now be set forth in detail with reference to the drawings.

Our preliminary experiments (Ding, Huxlin & Knox, 2007, Ding et al., 2008, Huxlin, Ding & Knox, 2008) showed that it is possible to change the refractive index of the lightly-fixed, mammalian cornea and lens without tissue destruction, a phenomenon we termed Intra-tissue Refractive Index Shaping (IRIS). To achieve this, we first measured, then reduced femtosecond laser pulse energies below the optical breakdown threshold of lightly-fixed post-mortem cat corneas and lenses. In both silicone and non-silicone-based hydrogels, this approach induced a significant change in refractive index without visible plasma luminescence or bubble formation (Ding et al., 2006).

Eight corneas and eight lenses were extracted under surgical anesthesia from five normal, adult domestic shorthair cats (*felis cattus*). To avoid decomposition and opacification prior to femtosecond laser micromachining, extracted feline tissues were immediately drop-fixed for 10 minutes (corneas) or one hour (lenses) in a solution consisting of 1% paraformaldehyde in 0.1M phosphate buffered saline (PBS), pH 7.4. Lenses were then cut into 500 µm thick slices using a HM650V vibratome (Microm International), after which lens sections and whole corneas (also ~500 µm thick) were immersed in a mixture of 30% ethylene glycol+ 30% sucrose in 0.1M PBS, pH7.4 at 4° C. Storage in this solution minimized tissue swelling and loss of transparency. Small pieces of tissue, ~1 $cm^2$ were then flattened onto a clear glass slide (1×3 inches, 1 mm thick, Surgipath Medical Industries Inc., IL). In the case of corneal pieces, this was done with the epithelium facing up and the endothelium facing down. A glass coverslip (Corning No. 0211 Zinc Titania glass) was placed on the top of each piece, stabilizing it for the duration of the experiment. The ethylene glycol/sucrose storage solution was used as mounting medium to minimize dehydration of the cornea and lens tissue samples since these effects are known to alter the refractive index and transparency of both these tissues (Fisher, Masiello, Goldstein & Hahn, 2003, Meek, Dennis & Khan, 2003, Patel, Alio & Perez-Santonja, 2004).

Femtosecond laser micro-machining was conducted as previously described in hydrogels (Ding et al., 2006). The laser source was a Kerr-lens mode-locked Ti:Sapphire laser (K-M Labs). The laser oscillator generated pulses averaging 300 mW, 27 fs in duration, with a 93 MHz repetition rate at 800 nm wavelength. A continuously variable, metallic, neutral density filter inserted into the optical path, was used to adjust the incident laser power onto each cat cornea and lens piece. Pulses were focused 100 µm below the tissue surface using a 60×, 0.70 NA Olympus LUCPlanFLN microscope objective with an adjustable working distance of 1.5-2.2 mm. Because the large amount of glass within the microscope objective induced significant chromatic dispersion into the femtosecond laser pulses, broadening the pulse durations, a standard extra-cavity-prism double-pass configuration was used to compensate for the dispersion and maintain the ultra-short pulse duration. By carefully adjusting this dispersion compensator, we obtained nearly transform-limited 27 fs duration pulses at the focal point of the focusing objective, as measured by a collinear auto-correlator using 3rd order surface harmonic generation (Meschulach, Barad & Silberberg, 2003, Squier, Fittinghoff, Barty, Wilson, Muller & Brakenhoff, 1998). During IRIS, the slide containing the biological tissue samples was mounted on a 3D scanning platform consisting of a Physik Instrumente P-622.2CD XY scanning stage with 250 µm travel range and 0.7 nm close-loop resolution, and a Newport VP-25XA linear servo Z-axis scanning stage with 25 mm travel range and 100 nm resolution. An infrared CCD camera was used to monitor the micromachining process and the generation of visible plasma luminescence in real-time.

Our first step was to establish thresholds for the optical breakdown of lightly-fixed feline cornea and lens. The neutral density filter was first adjusted to minimize the focused incident laser power on the cornea and the lens below their breakdown thresholds (Giguere et al., 2007, Loesel et al., 1996). Adjusting the neutral density filter then progressively increased the incident laser power. The breakdown threshold power was reached when visible plasma luminescence suddenly appeared and strong scattering light as well as laser-induced damage became visible (FIGS. 1A-1D). With our 0.70 NA long-working-distance objective, the measured breakdown thresholds for cat cornea and lens were ~55 mW and 75 mW average laser power respectively, which corresponds to pulse energies of 0.6 nJ and 0.8 nJ.

FIGS. 1A-1D: Femtosecond IRIS in lightly-fixed cat corneal stroma just around the tissue breakdown threshold. 1A,1C: Differential interference contrast (DIC) images of lines created in the stroma of two different, lightly-fixed cat corneas with 0.6 nJ pulses and a scanning speed of 10 µm/s. Note dark spots of tissue destruction and "bubbles" (arrowed) along the micromachined lines (clear, horizontal lines within stromal tissue). 1B,1D: Bright Field (BF) images of the corneal region in 1A,1C illustrating the visibility of dark spots of tissue destruction (arrowed) and the relative invisibility of the rest of the lines that are clearly seen under DIC conditions (see 1A,1C).

Figure 2A:
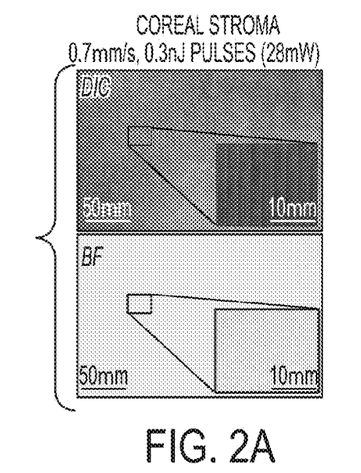
FIGS. 2A and 2B show femtosecond IRIS in a lightly fixed cat corneal stroma and lens cortex below the tissue breakdown threshold.
Figure 2B:
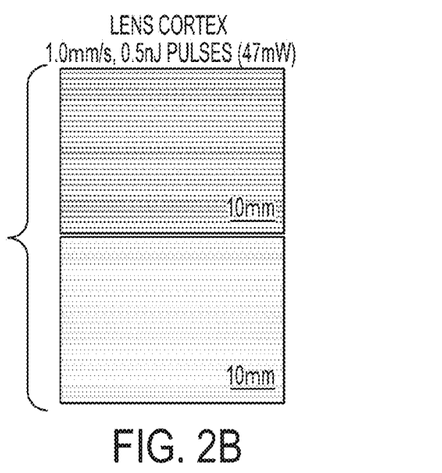

Once tissue breakdown thresholds were established, the focused laser power was lowered gradually by carefully adjusting the neutral density filter until lines could be micromachined without the induction of bubbles or burns (FIGS. 2A and 2B). Average laser power settings at which this could be done were 30 mW in the cornea and 45 mW in the lens, corresponding to pulse energies of about 0.3 nJ and 0.5 nJ respectively. These values lay between those used for imaging and our measured breakdown thresholds. The gratings were micromachined in the horizontal plane within the stromal layer of each corneal piece and the cortex of each lens at a constant speed of 0.7 µm/s for the cornea and 1 µm/s for the lens. The spherical aberration at the laser focus induced by refractive index mismatch was compensated by adjusting the correction collar of the focusing microscope objective in order to achieve the smallest possible laser-affected region along the laser propagation direction (Ding et al., 2006).

Figure 1A:
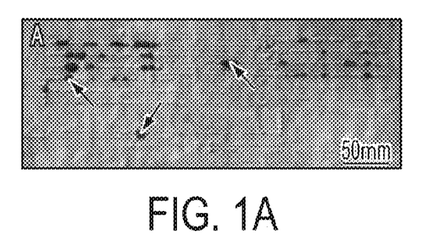
FIGS. 1A-1D show femtosecond IRIS in a lightly fixed cat corneal stroma just around the tissue breakdown threshold.
Figure 1B:
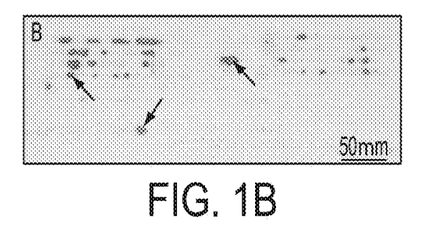
Figure 1C:
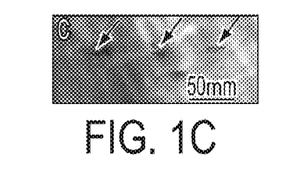
Figure 1D:
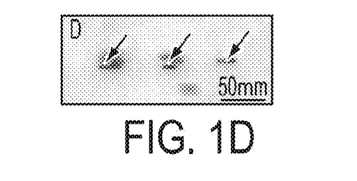

Exposure of lightly-fixed cat corneal and lenticular tissue to 0.3 nJ or 0.5 nJ femtosecond laser pulses (28 mW or 47 mW average laser power) respectively resulted in the reliable creation of line gratings about 100 µm below the epithelial surface or 100 µm below the lens surface in all test samples (FIGS. 2A and 2B). When imaged immediately after micromachining, individual grating lines could be clearly observed and distinguished with differential interference contrast (DIC) microscopy, but they were practically invisible when viewed under bright field (BF) transmission microscopy (BF images in FIGS. 2A and 2B). This could be interpreted as the grating lines having very low scattering properties, which is in contrast to the destructive tissue changes observed with laser pulse energies above the optical breakdown threshold of the tissues (FIGS. 1A-1C). Using the knife-edge method (Smith, 2000), we ascertained that the laser focus diameter was 2.5 µm in air, which was much bigger than the micromachined line-widths. Thus, it appears that only the central part of the laser focal area had sufficient intensity to modify corneal and lens tissues.

FIGS. 2A and 2B: Femtosecond IRIS in lightly-fixed cat corneal stroma and lens cortex below the tissue breakdown threshold. 2A: The top photomicrographs are DIC images of a periodic line grating created using 0.3 nJ pulses and a scanning speed of 0.7 µm/s into the stromal layer of a cat corneal piece. Note the absence of tissue destruction (no brown spots). The insert shows a magnified portion of the grating. The bottom photographs are bright field (BF) images of the corneal regions shown the DIC pictures. Note the poor visibility of the micromachined gratings under transmitted, bright light microscopy, which contrasts with the high visibility of the brown spots created when using laser power above the tissue breakdown threshold (see FIGS. 1A-1C). 2B: DIC image of a periodic line grating created using 0.5 nJ pulses and a scanning speed of 1 µm/s in a piece of lens cortex. Note the absence of tissue destruction (no brown spots). The BF image shows the lens region illustrated in the DIC picture.

To assess whether the gratings generated in corneal and lens pieces were associated with a change in refractive index, the slides containing the tissue were first placed under an Olympus BX51 optical microscope where gratings were localized using DIC imaging. A low-power 632.8 nm He—Ne laser was then used to irradiate the gratings (FIGS. 3A and 3B), generating a diffraction pattern that was captured by a digital camera and used to calculate the refractive index changes attained, as described previously (Ding et al., 2006).

Figure 3A:
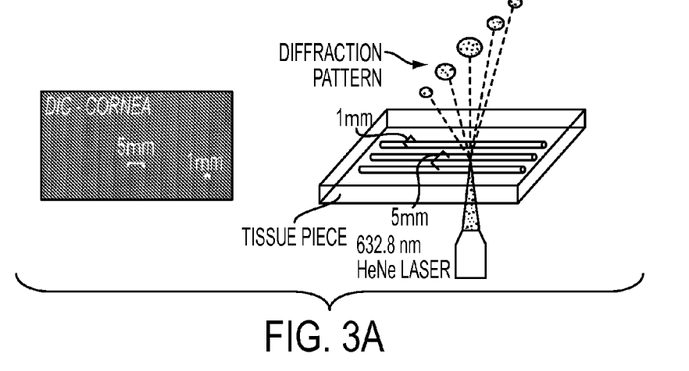
FIGS. 3A and 3B show measurement of the refractive index change in IRIS-treated corneas and lenses immediately after the treatment.
Figure 3B:
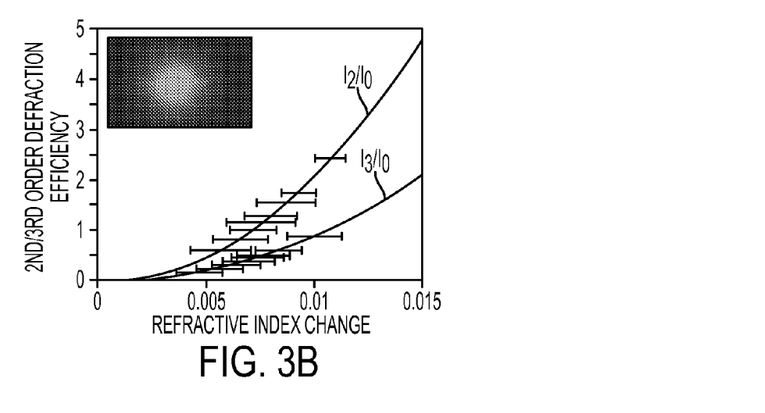

FIGS. 3A and 3B. Measuring refractive index change in IRIS-treated corneas and lenses immediately after the treatment. 3A: DIC image of a periodic line grating created using 0.3 nJ pulses and a scanning speed of 0.7 µm/s in the stromal layer of a piece of cat cornea and subsequently illuminated with a 632.8 nm He—Ne laser to generate diffraction patterns (as shown in 3B) that were used to calculate the change in refractive index attained. 3B: Graph plotting the 2nd and 3rd order diffraction efficiencies and the corresponding laser-induced refractive index changes of eight gratings micromachined in different corneal samples immediately after they were created. The insert is a photograph of the diffraction pattern obtained when illuminating the grating shown in A with a 632.8 nm He—Ne laser.

In brief, a power meter measured the intensity of the $0^{th}$-$3^{rd}$ order diffracted light from the gratings and the different order diffraction efficiencies were obtained by calculating the ratios between the intensity of the $1^{st}$, $2^{nd}$ and $3^{rd}$ to the $0^{th}$ order diffraction light. Since the intensity distribution of the diffraction pattern of a phase grating is proportional to the square value of the Fourier Transform of the transmittance function of the grating (Born & Wolf, 1970), one particular value of refractive index change matches only one particular diffraction efficiency value (Ding et al., 2006). To reduce measurement error of the diffraction order intensities, we collected five measurements on each grating, calculating the average value obtained and its standard deviation. In principle, the spatial distribution of the refractive index change within the micromachined region was a small-scale gradient-index structure. However, for the purpose of the present investigation, we presumed the index profile to be uniform within the grating lines, which were only 3 µm deep because the spherical aberration at the focal point was corrected (Ding et al., 2006).

Because displacement of the stromal collagen lamellae as a result of post-mortem corneal swelling could not be completely avoided the scattering effect from the $0^{th}$ order diffraction light was very strong obscuring the $1^{st}$ order diffraction light (Meek et al., 2003). Thus, only the $2^{nd}$ and $3^{rd}$ order diffraction efficiencies of each grating could be measured and used to calculate an approximate refractive index change in corneal pieces (FIG. 3B). Because tissue swelling and opacification were minimal in slices of lens cortex, the $0^{th}$ through $3^{rd}$ order diffraction light could be measured clearly and $1^{st}$ and $2^{nd}$ order diffraction efficiencies were used to calculate the induced refractive index change. Although single diffraction efficiency is usually sufficient to calculate refractive index, here we measured $1^{st}/2^{nd}$ or $2^{nd}/3^{rd}$ combinations to confirm that the index changes calculated were consistent through different diffraction orders, assuming that the refractive index of cat corneal stroma and lens cortex were 1.376 and 1.400 respectively (Hughes, 1977). For corneal stroma, the index changes induced by the laser in our multiple samples ranged between 0.0050.001 and 0.01±0.001 (FIG. 3B). For cat lens cortex, index changes were larger, ranging between 0.015±0.001 and 0.021±0.001.

After micromachining, each cornea and lens piece was stored in the ethylene glycol sucrose solution at 4° C. After one month, each piece was re-mounted onto a new glass slide for imaging and a repeat of the diffraction light intensity measurements. This allowed us to assess whether the RI change initially observed had been maintained during storage. Our first observation was that although the storage solution significantly slowed corneal swelling and opacification, it did not completely prevent either. In spite of this, DIC microscopy was able to reveal the grating structures initially micromachined (FIG. 4A).

Figure 4A:
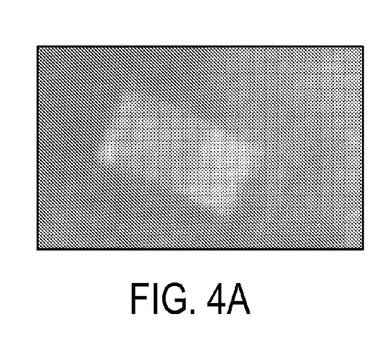
FIGS. 4A and 4B show measurement of the refractive index change in IRIS-treated corneas one month after the treatment.
Figure 4B:
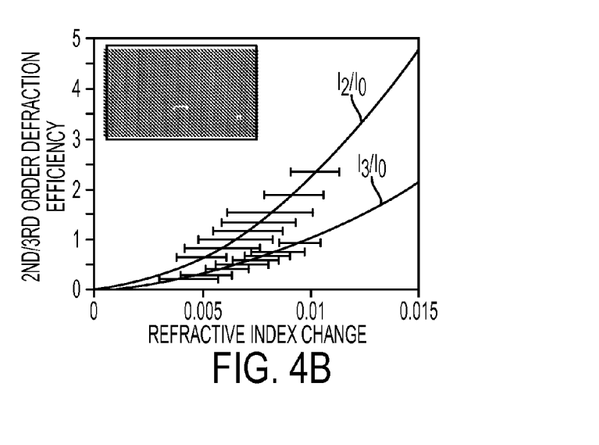

FIGS. 4A and 4B: Measuring refractive index change in IRIS-treated corneas 1 month after the treatment. 4A: DIC image of a periodic line grating created using 0.3 nJ pulses and a scanning speed of 0.7 µm/s into the stromal layer of the cat corneal piece shown in FIGS. 3A and 3B and stored for 1 month. The grating is still visible, but the clarity of its lines is decreased, a likely result of corneal swelling and opacification. 4B: Graph plotting the diffraction efficiencies and the corresponding refractive index changes of eight gratings measured one month after they were created in 8 different corneal pieces. The insert is a photograph of the diffraction pattern obtained when illuminating the grating shown in FIG. 4A with a 632.8 nm He—Ne laser.

For both corneal and lens slices, the diffraction light distribution of one-month old gratings (FIG. 4B) was not significantly different than that obtained right after the gratings' creation (FIG. 3B). In the corneal pieces, the scattering light from the $0^{th}$ order diffraction still obscured the order diffraction. However, the $2^{nd}$, $3^{rd}$, and even $4^{th}$ order diffractions were visible and measurable. In the lens pieces, the $1^{st}$, $2^{nd}$ and $3^{rd}$ order diffraction were visible. The refractive index change after one month of storage still ranged between 0.005±0.001 and 0.01±0.001 for corneal pieces and between 0.015±0.001 and 0.021±0.001 for lens slices.

Potentiating IRIS by increasing two-photon absorption (TPA) or other multi-photon absorption of the cornea and lens will now be disclosed. In our early work with native hydrogels, femtosecond micromachining caused index changes in the range of +0.02 to +0.06, with very slow scanning speeds, as slow as 0.4 microns per second (Ding et al., 2006). The index changes attained in the cat cornea were small (~0.005-0.01) and background scattering made the features difficult to detect. We wrote larger index changes in 500 µm thick slices of cat lens (~0.015-0.021), but all at very low scanning speeds (0.7 to 1 µm/s). Such slow scanning speeds severely limit the applicability of the IRIS technique, since the writing of any 3D feature within biological materials would take a prohibitively long time under these conditions.

Figure 4C:
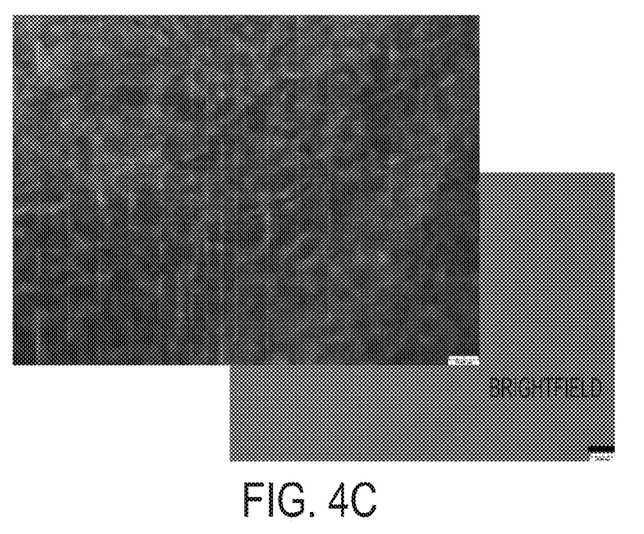
FIGS. 4C-4F show micromachining results in a cornea and a lens with Na-Fluorescein doping.
Figure 4D:
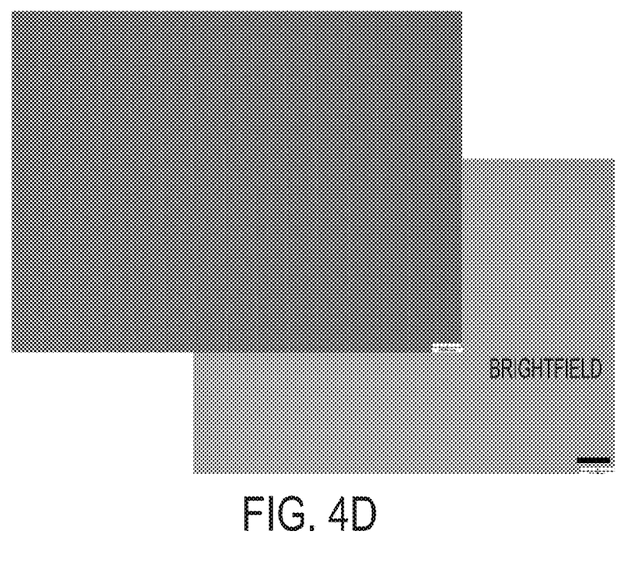
Figure 4E:
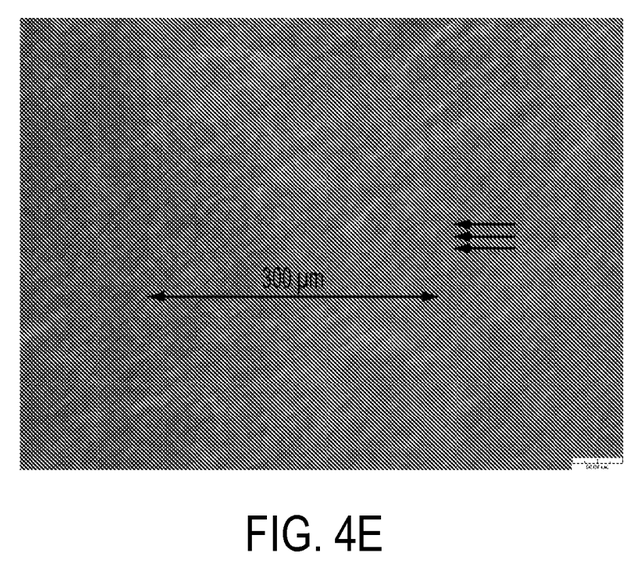
Figure 4F:
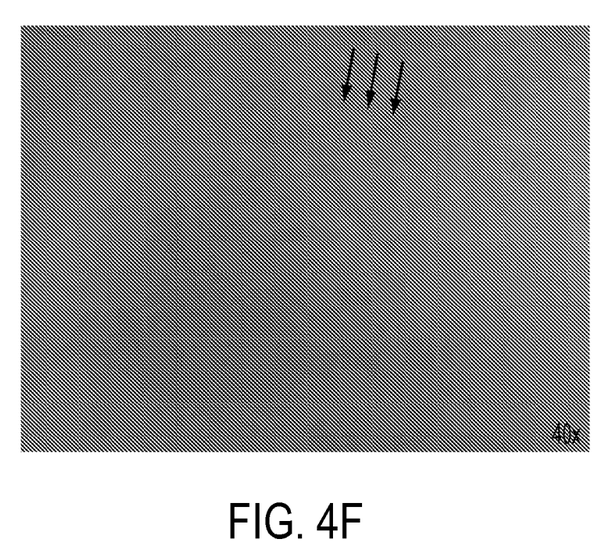

The major reason why writing speeds need to be so slow in the cornea and the lens is that these clear biological tissues possess natively low two-photon absorption (TPA) properties. Thus, we hypothesized that if the TPA of cornea and lens could be increased through the incorporation of a two-photon absorbing chromophore, this should theoretically increase the rate and magnitude of IRIS in these tissues. Sodium Fluorescein is one such chromophore, which is already commonly used in ophthalmic (and medical) practice. It is non-toxic to the living eye and can even be injected intravenously (e.g. for retinal angiography). To test our hypothesis, we incubated lightly-fixed cornea and lens pieces in a 25% solution of Sodium Fluorescein in ethylene glycol/sucrose/PBS overnight. Both tissue types readily absorbed the chromophore and turned slightly orange. They were then rinsed and IRIS was performed as described above. In Fluorescein-treated cat corneas, scanning speeds of 1 mm/s (~1,400× faster than in non-treated corneas) were attained and used to create multiple lines that were several mm long, and whose refractive index change averaged 0.02 (up to 4× larger than in non-treated corneas). Just as in the non-fluorescein treated corneas, these features were long-lived, lasting through several months of refrigerated storage. FIG. 4C is a phase contrast image showing the refractive index change lines in a cornea doped with 25% sodium fluorescein after micromachining with a scanning speed of 1 mm/s, an average power of 120 mW, a depth below the surface of 120 µm, and a laser wavelength of 800 nm. FIG. 4D is a phase contrast image showing the refractive index change lines in an intraocular lens doped with 25% sodium fluorescein after micromachining with a scanning speed of 1 mm/s, an average power of 100 mW, a depth below the surface of 120 µm, and a laser wavelength of 800 nm. FIG. 4E is a phase contrast image showing a 300 µm wide band micromachined in a doped cat cornea 100 µm below the surface using 20 fs laser pulses, a scanning speed of 1 mm/s, an average power of 120 mW, and a laser wavelength of 800 nm. The image in FIG. 4E was taken right after micromachining. FIG. 4F is an image taken after the fluorescein has been rinsed off.

Femtosecond laser treatment is performed under surgical or topical anesthesia as previously described for conventional laser refractive surgery (Bühren, Yoon, Kenner, MacRae & Huxlin, 2007b, Nagy et al., 2007). The subjects are placed into a specially designed head-mount, which will hold them in a supine position, with the eyes facing directly upwards. A drop of 0.5% Proparacaine Hydrochloride (or other ophthalmic anesthetic agent) will be placed in the eye to be treated. One to two drops of 20% NaFluorescein in a 10% solution of dimethyl sulfoxide (DMSO) in Celluvisc will also be administered to each eye to be treated in order to increase the two-photon absorption rate of the cornea. Our pilot experiments show that 10 minutes is sufficient to allow penetration of the fluorescein chromophore through the entire thickness of the cornea (see FIGS. 5A and 5B). Lower and higher concentrations of Na Fluorescein also work, but the amount of time required for penetration increases at lower concentrations. The corneal surface can then be kept moist with the application of saline or ophthalmic moistening agents. Once corneal reflexes have disappeared, the subject can then undergo IRIS treatment over a circular (or otherwise shaped) area 6 mm (or other dimensions, as required) in diameter, in the center (or other location) of its cornea, at a depth of 100 µm (or other depths) below or within the surface epithelium. Other positional parameters can be used if needed. The eye can be kept immobile during the laser treatment by a fixation target or by conjunctival structures, which will be removed at the end of the operation. An infrared CCD camera is used to monitor the micromachining process and the generation of visible plasma luminescence in real-time. The treatment should take about 5-10 minutes per eye, after which the subject will be recovered as clinically prescribed.

Figure 5A:
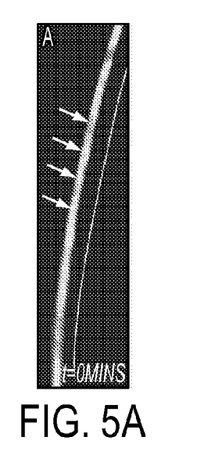
FIGS. 5A and 5B show slit lamp imaging of the cornea, showing the penetration of a chromophore.
Figure 5B:
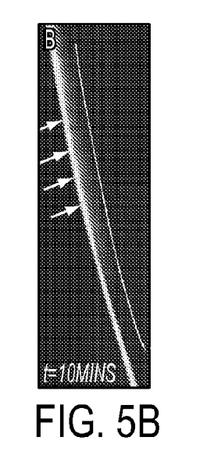

FIGS. 5A and 5B: Slit lamp imaging of the cornea of an anesthetized cat with Fluorescein filter, demonstrating penetration of NaFluorescein into the stroma within 10 minutes of its topical application to the eye. 5A. Slit lamp image taken immediately after application of 25% NaFluorescein to the ocular surface. Only the surface epithelium (arrowed) stained. The rest of the corneal depth (approx. to the dotted white line) is completely black. 5B. Slit lamp image of the cornea in FIG. 5A, taken 10 minutes later. The epithelium (arrowed) is still labeled, but now Fluorescein can be seen deeper in the stroma, almost to the endothelium (~dotted line).

A similar protocol, with the major difference being that the Na Fluorescein solution might have to be injected into the anterior chamber of the eye, could be used to enhance TPA in the living lens. IRIS could be performed in the lens by simply using a longer-working-distance focusing objective to focus the femtosecond laser beam into the lens in situ.

In order to assess whether chemical fixation of the cornea with paraformaldehyde was critical to attaining IRIS in the cornea, we recently performed IRIS on a non-fixed (fresh), post-mortem cat cornea immediately after enucleation. Several small gratings were inscribed one above the other in the corneal stroma and they were imaging with optical coherence tomography (OCT). The reason we stacked several gratings together was in order to make sure that our OCT, with its resolution of ~10 µm, could actually resolve these features, given that individual IRIS lines were only 1-3 µm thick. We reported on the results of this experiment at the recent ARVO meeting (Huxlin et al., 2008) and are providing some pictures in FIGS. 6A-6C. Thus, while fixation may influence the magnitude of RI change attained, IRIS does not actually require it.

Figure 6A:
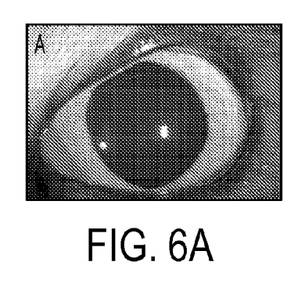
FIGS. 6A-6C show IRIS in the unfixed cat cornea.
Figure 6B:
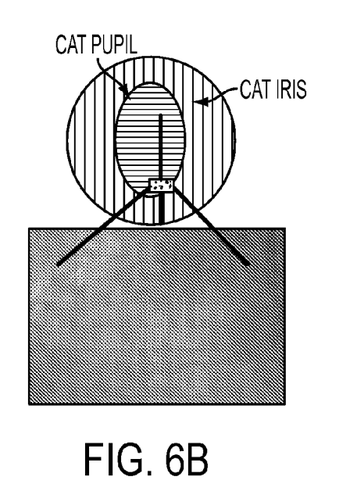
Figure 6C:
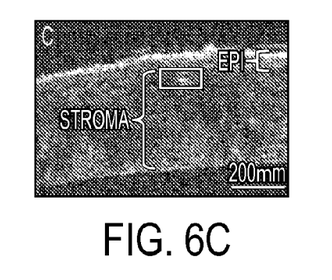

FIGS. 6A-6C: IRIS in the unfixed cat cornea. 6A. Front view of the cat eye just prior to excision of the globe. 6B. Schematic diagram of the view of the eye shown in FIG. 6A, illustrating the different visible features (cat iris and pupil) as well as the location of the femtosecond treatment (magnified below in DIC mode) at the bottom of the cornea. The long, black, vertical line through the rectangular IRIS pattern indicates the imaging plane used for optical coherence tomography (OCT). 6C. OCT image of the corneal layers collected through the rectangular IRIS grating (in the plane of the thin black vertical line in FIG. 6B). The IRIS pattern is visible as a thin, horizontal line of increased reflectivity (inside the white rectangle) within the corneal stroma, about 200 µm below the epithelial (epi) surface.

IRIS does not change the Raman spectrum of hydrogels—changes in refractive index, not material composition or chemistry. Balafilcon A hydrogel polymer (Bausch & Lomb, USA) was used for this experiment, whose goal to was to gain insight into the mechanisms by which femtosecond micromachining achieved its refractive index change in hydrated, optically clear but non-biological materials. The chemical components of the hydrogel used (Balafilicon A) included tris-(trimethylsiloxy)-silyl propylvinyl carbamate (TPVC), N-vinyl pyrrolidone (NVP) and other types of silicones (Karlgard, Sarkar, Jones, Moresoli & Leung, 2004). Balafilcon A contains 36% water by weight and has an average refractive index of 1.4220 (Ding et al., 2006). The cutoff wavelength of its transmission spectra are within the range of 300 to 350 nm, and its transmissivity at 800 nm is ~83% (Ding et al., 2006). A Kerr-lens mode-locked Ti:Sapphire femtosecond laser oscillator (K-M Labs), generating pulses of 300 mW average power, 27 fs pulsewidth and 93 MHz repetition rate at 800 nm was focused into the hydrogels using a 60×0.70 NA Olympus LUCPlanFLN long-working-distance objective. Throughout the whole experimental process, the hydrogel samples were mounted in a Borate Buffered Saline (BBS) solution between two cover glass slides and maintained their water-content. A 3D scanning platform formed by three Newport VP-25XA linear servo stages with 100 nm resolution was employed to move the hydrogel samples transversely to the direction of the laser beam. Smooth lines 40 µm long were inscribed just below the hydrogel surface using 1.3 nJ pulse-energies, which were below the optical breakdown threshold of the material. These low pulse-energies created a 0.06 refractive index change along the lines. Using the same knife edge method reported previously (Ding et al., 2006), we measured a laser focal diameter of about 2.5 µm. This focal diameter gave rise to laser-irradiated lines about 1 µm wide and 3 µm deep.

Figure 7A:
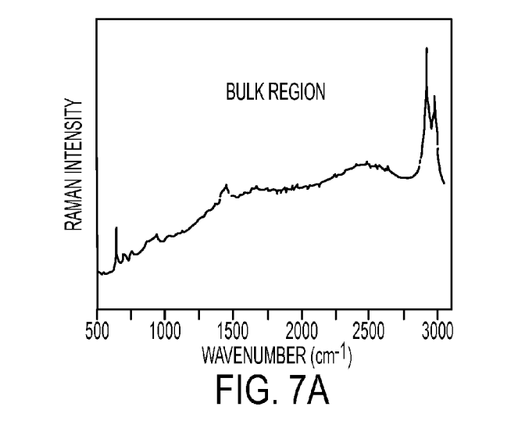
FIGS. 7A-7D show the effects on the Raman spectrum.
Figure 7B:
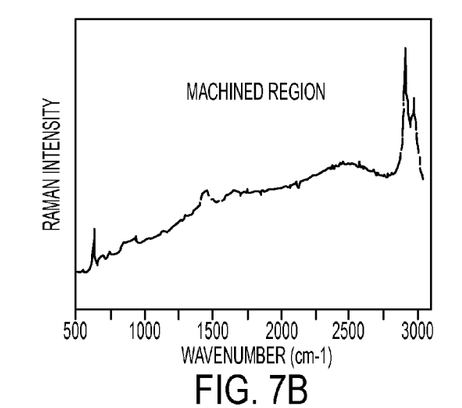
Figure 7C:
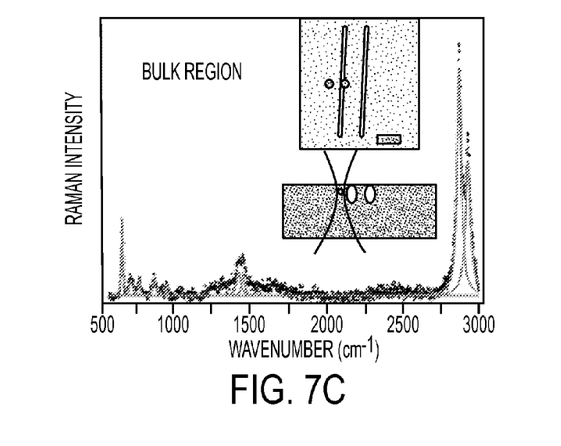

In order to check for structural modifications in the machined region, several Raman spectra were measured in 400 nm steps both within and next to the micromachined lines using a 3 mW, 632.8 nm HeNe laser. In both spectra, several Raman peaks were detected over the broad background fluorescence (FIGS. 7A, B). Differences in the background fluorescence of the two spectra were first measured since some of the defects generated by MHz femtosecond laser pulses are known to increase fluorescence intensity in fused silica (Reichman, Krol, Shah, Yoshino, Arai, Eaton & Herman, 2006). Here however, no. significant changes in background fluorescence were detected. The Raman signal was then calculated by subtracting the background fluorescence from the original spectrum (FIGS. 7C, D). The Raman peaks could be assigned to different material bonds activities (see FIG. 7D), but most importantly, the Raman spectra obtained from the machined region were almost identical to the Raman spectra obtained from the untreated regions of hydrogel, suggesting that the micromachining process did not induce significant structural and chemical changes in the hydrogel polymer.

Figure 7D:
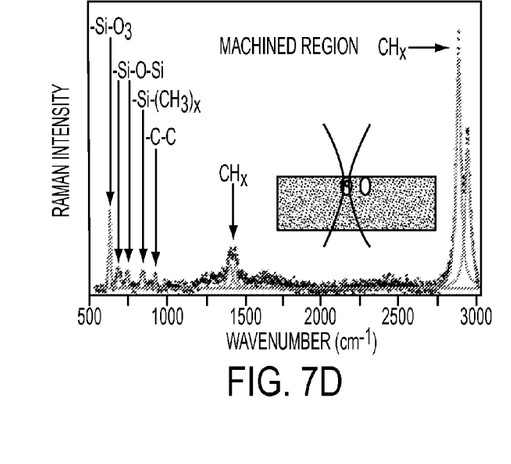

FIG. 7A. Raman spectrum of an untreated (bulk) region of Balafilcon A hydrogel in BBS solution, showing significant background fluorescence over which spectral peaks are superimposed. FIG. 7B. Raman spectrum of one of the fs laser-modified lines inside a Balafilcon A hydrogel piece (see insets in FIG. 7C). FIG. 7C. Raman spectrum of the untreated bulk region of the Balafilcon A hydrogel imaged in FIG. 7A, with background correction. The lower insert illustrates the plane of Raman imaging in a schematic cross section of the modified hydrogel piece photographed above it. The photograph inset is a DIC image of the two micromachined lines. Scale bar=10 µm. FIG. 7D. Raman spectrum of one of the micromachined lines with background correction, showing peaks that are identical in location and magnitude to the adjacent, bulk region imaged in FIG. 7C.

Figure 8A:
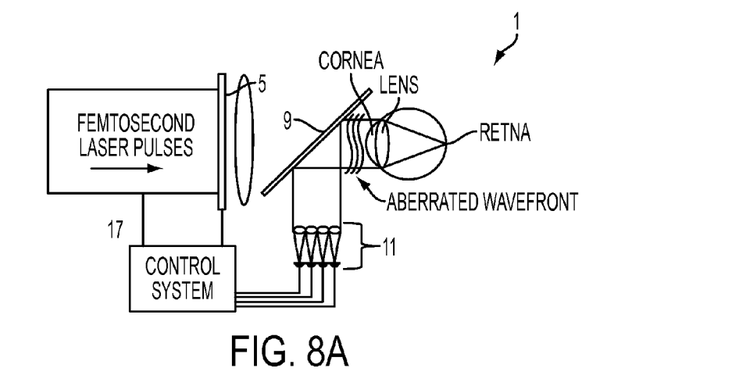
FIGS. 8A-8C show a device on which the preferred or another embodiment can be implemented.
Figure 8B:
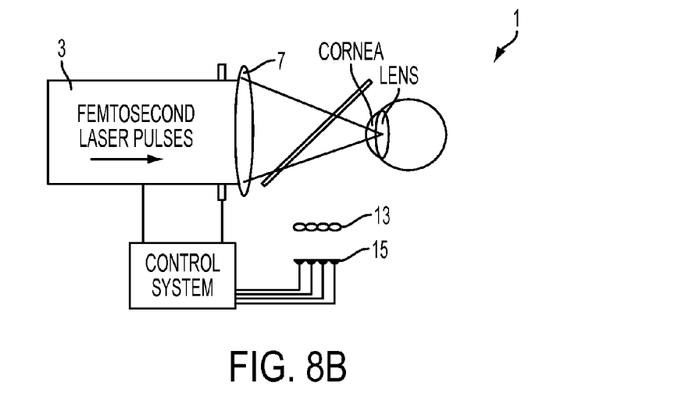
Figure 8C:
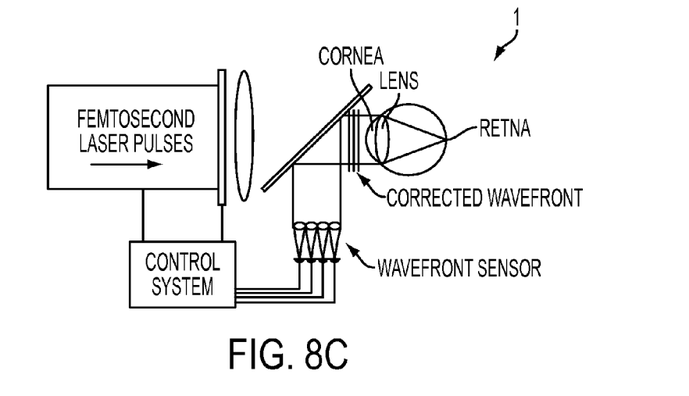

FIGS. 8A-8C show a schematic diagram of a device 1 used to carry out the preferred embodiment or another embodiment. The device 1 includes a laser 3 for emitting femtosecond laser pulses, a shutter 5, a focusing lens 7, a dichroic mirror 9, a wavefront sensor 11 having a lenslet array 13 and a detector array 15, and a control system 17 for controlling the operations described herein.

As illustrated in FIGS. 8A-8C, the process we propose would include the following steps: (1) using a wavefront sensor to detect and measure the lower and higher order aberrations along the optical path of a given eye, (2) calculating the topography and magnitude of refractive index changes required to achieve the necessary aberration correction, (3) focusing the femtosecond laser pulses either into the cornea or intraocular lens in order to carry out the micromachining necessary to induce the required refractive index change. Once the micromachining is complete, the wavefront sensor would be used once again to check the correction of the ocular wavefront. Since the resolution of the femtosecond laser micromachining is about 1 µm, this noninvasive method could be used as a complement or an alternative method for current customized wavefront correction methods.

In FIG. 8A, the shutter 5 is closed for detection of wavefront aberration from the optical path through the wavefront sensor 11, using aberrated light A reflected from the retina R of the eye E. In FIG. 8B, the shutter is open, and light pulses P from the femtosecond laser 3 are used to correct the aberration by locally changing the index in the cornea C or the lens L. In FIG. 8C, after femtosecond laser micromachining, the wavefront correction is verified once again using the wavefront sensor.

While a preferred embodiment has been set forth in detail above, those skilled in the art who have reviewed the present disclosure will readily appreciate that other embodiments can be realized within the scope of the invention. For example, numerical values are illustrative rather than limiting, as are recitations of specific equipment and sources. Also, while the preferred embodiment has been disclosed in terms of two-photon absorption, the invention can be implemented through absorption of three or more photons. Therefore, the present invention should be construed as limited only by the appended claims.

We claim:

1. A method for micromachining a living or fixed ocular tissue, the method comprising:
    (a) applying a multiple-photon-absorbing chromophore to the living or fixed ocular tissue;
    (b) providing a laser and emitting laser pulses therefrom at a wavelength in the visible or near-infrared range, a pulse width of between 5 fs and 1 ps, a frequency between 1 MHz and 10 GHz, an average power between 1 mW and 1,000 mW, and an intensity high enough to change the refractive index of a focus spot in the ocular tissue, but not high enough to destroy the ocular tissue;
    (c) directing said pulses at the ocular tissue and focusing said pulses to form said focus spot such that said multiple-photon-absorbing chromophore undergoes multiple-photon absorption, wherein a size of the focus spot is between 0.5 µm and 50 µm; and
    (d) changing the refractive index of the ocular tissue at locations defined by the focus spot, using the multiple-photon absorption caused by the pulses,
    wherein the ocular tissue comprises tissue of a lens or tissue of a cornea.

2. The method of claim 1, wherein the multiple-photon-absorbing chromophore comprises a two-photon-absorbing chromophore, and wherein, in step (c), the multiple-photon-absorbing chromophore undergoes two-photon absorption.

3. The method of claim 2, wherein the two-photon-absorbing chromophore comprises sodium flourescein.

4. The method of claim 1, wherein the ocular tissue comprises tissue of a lens.

5. The method of claim 1, wherein the ocular tissue comprises tissue of a cornea.

6. The method of claim 1, wherein the locations defined by the focus spot are selected to form a structure selected from the group consisting of Bragg gratings, microlens arrays, zone plates, and Fresnel lenses.

7. The method of claim 1, wherein the frequency is between 10 MHz and 500 MHz.

8. The method of claim 1, wherein the pulse width is between 10 fs and 100 fs.

9. The method of claim 1, wherein the average power is between 10 mW and 100 mW.

10. The method of claim 9, wherein the average power is between 50 mW and 60 mW.

11. The method of claim 1, wherein the laser pulses have a pulse energy between 0.01 nJ and 10 nJ.

12. The method of claim 11, wherein the laser pulses have a pulse energy between 0.1 nJ and 2 nJ.

13. The method of claim 1, wherein the size of the focus spot is between 0.5 µm and 10 µm.

14. The method of claim 13, wherein the size of the focus spot is between 0.5 µm and 2 µm.

15. The method of claim 1, wherein the focus spot is scanned at a scanning speed between 0.1 µm/s and 10 mm/s.

16. The method of claim 1, wherein the laser pulses have a wavelength between 600 nm and 1,000 nm.

17. The method of claim 16, wherein the wavelength is between 700 nm and 900 nm.

18. The method of claim 1, wherein the laser pulses have a wavelength in the near-infrared range above 1,000 nm.

19. The method of claim 1, wherein the pulse width is between 10 fs and 100 fs, the frequency is between 10 MHz and 500 MHz, the average power is between 10 mW and 100 mW, and the laser pulses have a pulse energy between 0.1 nJ and 2 nJ.

20. The method of claim 19, wherein the focus spot is scanned at a scanning speed attaining 1 mm/s.

21. The method of claim 20, wherein the focus spot is scanned at a scanning speed between 1 mm/s and 10 mm/s.

22. The method of claim 1, wherein the focus spot is scanned at a scanning speed attaining 1 mm/s.

23. The method of claim 1, further comprising using a wavefront sensor to detect and measure lower and higher order aberrations along an optical path of a given eye, and calculating a topography and magnitude of refractive index changes required to achieve an aberration correction, and wherein the laser pulses are focused either into the tissue of a lens or tissue of a cornea of the given eye in order to carry out micromachining necessary to induce the required refractive index change.

24. The method of claim 23, wherein the laser pulses are focused into the tissue of a cornea of the given eye in order to carry out micromachining necessary to induce the required refractive index change.

25. The method of claim 24, wherein an anesthetic and sodium flourescein are applied to the given eye before carrying out the micromachining, and the laser pulses have a wavelength between 600 nm and 1,000 nm and a pulse width between 10 fs and 100 fs.

26. The method of claim 23, wherein once the micromachining is complete, a wavefront sensor is used to check the correction of the ocular wavefront.

27. The method of claim 1, wherein the changing the refractive index of the tissue at locations defined by the focus spot creates corneal fiducial markings for aligning eye trackers during laser refractive surgery.

* * * * *

UNITED STATES PATENT AND TRADEMARK OFFICE
CERTIFICATE OF CORRECTION

| | |
|---|---|
| PATENT NO. | : 9,545,340 B1 |
| APPLICATION NO. | : 12/207137 |
| DATED | : January 17, 2017 |
| INVENTOR(S) | : Wayne H. Knox, Krystel R. Huxlin and Li Ding |

It is certified that error appears in the above-identified patent and that said Letters Patent is hereby corrected as shown below:

In the Specification

In Column 1, Lines 18-20, (approx.), under the heading "Statement of Government Interest" delete: "The work leading to the present invention was supported in part by NIH Grant Nos. R01 EY015836 and 08P0EY01319F."

And replace with:
--This invention was made with government support under Grant Numbers EY015836 and EY001319 awarded by the National Institutes of Health.--

Signed and Sealed this
Sixth Day of June, 2017

Michelle K. Lee
*Director of the United States Patent and Trademark Office*